(12) United States Patent
Brockman et al.

(10) Patent No.: US 10,472,380 B2
(45) Date of Patent: Nov. 12, 2019

(54) PLATINUM COMPOUNDS HAVING A HETEROCYCLE LIGAND, NANOPARTICLES, AND USES THEREOF

(71) Applicant: PLACON THERAPEUTICS, INC., Watertown, MA (US)

(72) Inventors: Adam H. Brockman, Arlington, MA (US); Mark T. Bilodeau, Waltham, MA (US); Benoît Moreau, Newton, MA (US); Edward R. Lee, Sudbury, MA (US)

(73) Assignee: PLACON THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/685,440

(22) Filed: Aug. 24, 2017

(65) Prior Publication Data

US 2017/0349615 A1 Dec. 7, 2017

Related U.S. Application Data

(62) Division of application No. 14/905,537, filed as application No. PCT/US2014/046873 on Jul. 16, 2014, now Pat. No. 9,771,387.

(60) Provisional application No. 61/846,708, filed on Jul. 16, 2013.

(51) Int. Cl.
| | |
|---|---|
| C07F 15/00 | (2006.01) |
| A61K 31/555 | (2006.01) |
| A61K 9/00 | (2006.01) |
| A61K 9/51 | (2006.01) |

(52) U.S. Cl.
CPC ........ *C07F 15/0093* (2013.01); *A61K 9/0019* (2013.01); *A61K 9/5153* (2013.01); *A61K 31/555* (2013.01); *A61K 9/5146* (2013.01)

(58) Field of Classification Search
None
See application file for complete search history.

(56) References Cited

U.S. PATENT DOCUMENTS

| | | |
|---|---|---|
| 5,665,771 A | 9/1997 | Murrer |
| 6,340,770 B1 | 1/2002 | Kwon et al. |
| 2007/0082882 A1 | 4/2007 | Farrell |

FOREIGN PATENT DOCUMENTS

| | | |
|---|---|---|
| EP | 0 328 274 A1 | 8/1989 |

OTHER PUBLICATIONS

International Search Report and Written Opinion dated Nov. 7, 2014 in International Application No. PCT/US2014/046873, entitled "Platinum Compounds Having a Heterocycle Ligand, Nanoparticles, and Uses Thereof."
Park, G.Y. et al., "Phenanthriplatin, a monofunctional DNA-binding platinum anticancer drug candidate with unusual potency and cellular activity profile" (2012) PNAS 109(30):11987-11992.

*Primary Examiner* — Craig D Ricci
(74) *Attorney, Agent, or Firm* — DT Ward, PC; Donna T. Ward; Heng Zhu

(57) ABSTRACT

The present disclosure relates to novel platinum compositions having a heterocycle ligand and nanoparticles and methods using such compositions, e.g. for treating cancer.

1 Claim, No Drawings

PLATINUM COMPOUNDS HAVING A HETEROCYCLE LIGAND, NANOPARTICLES, AND USES THEREOF

CROSS REFERENCE TO RELATED APPLICATIONS

This application is a Divisional application of U.S. Ser. No. 14/905,537 filed Jan. 15, 2016, which is a 35 U.S.C. § 371 U.S. National Stage Entry of International Application No. PCT/US2014/046873 filed Jul. 16, 2014, which claims the benefit of priority of U.S. Application No. 61/846,708 filed Jul. 16, 2013, the contents of each of which are each incorporated herein by reference in their entirety.

FIELD OF INVENTION

The present disclosure relates to platinum based compounds and nanoparticles containing such compounds.

BACKGROUND

Platinum-based drugs are among the most active and widely used anticancer agents and cisplatin represents one of three FDA-approved, platinum-based cancer chemotherapeutics. Although cisplatin is effective against a number of solid tumors, especially testicular and ovarian cancer, its clinical use has been limited because of its toxic effects as well as the intrinsic and acquired resistance of some tumors to this drug. To overcome these limitations, platinum analogs with lower toxicity and greater activity in cisplatin-resistant tumors have been developed and tested, resulting in the approval of carboplatin and oxaliplatin in the United States. Carboplatin is generally less nephrotoxic, and oxaliplatin exhibits a different anticancer spectrum from that of cisplatin. Oxaliplatin has been approved as the first or second line therapy in combination with 5-fluorouracil/leucovorin for advanced colorectal cancer, for which cisplatin and carboplatin are essentially inactive. These platinum drugs have platinum in the $2^+$ oxidative state (Pt(II)).

Novel developments in nanomedicine are directed towards improving the pharmaceutical properties of the drugs and enhancing the targeted delivery in a cell-specific manner. Several cell-specific drugs are known in literature, and include monoclonal antibodies, aptamers, peptides, and small molecules. Despite some of the potential advantages of these drugs, disadvantages have limited their clinical application. Such disadvantages include size, stability, manufacturing cost, immunogenicity, poor pharmacokinetics and other factors.

However, nanoparticulate drug delivery systems are attractive for systemic drug delivery because of their ability to prolong drug circulation half-life, reduce non-specific uptake, and better accumulate at the tumors through an enhanced permeation and retention (EPR) effect. As a result, several therapeutic nanoparticles, such as Doxil® and Abraxane®, are used as the frontline therapies. Nevertheless, research efforts have heretofore focused on single or multiple drug encapsulations or tethering without cell-specific targeting moieties. The development of nanotechnologies for effective delivery of drugs or drug candidates to specific diseased cells and tissues, e.g., to cancer cells, in specific organs or tissues, in a tempospatially regulated manner can potentially overcome the therapeutic challenges faced to date.

SUMMARY OF INVENTION

The present teachings relate to compositions termed herein "platinum heterocycle" compounds, e.g., platinum compounds that include a phenanthridine moiety. Such compounds are useful, for example, for reducing, disrupting, or inhibiting the growth of a cancer cell or inducing the death of a cancer cell.

In various embodiments, the present teachings provide a compound of Formula I:

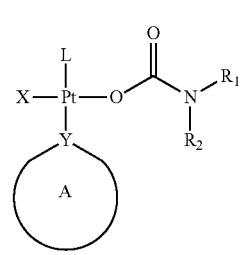

wherein:

X is a halide, carboxylate, carbonate, carbamate, sulfonate, sulfate, or phosphate;

L each is an independently amine or an independently substituted amine;

Y is selected from Nitrogen, Phosphorus, Oxygen and Sulfur;

A together with Y form a heteroaromatic optionally substituted with one or more substituents each independently selected from halogen, cyano, nitro, hydroxyl, ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide, wherein each of the ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide is optionally substituted with one or more suitable substituents; and wherein X and L form a bidentate ligand, or A together with Y or X form a bidentate ligand.

$R_1$ and $R_2$ are each independently H, alkyl, aryl and heteroaryl wherein each of the H, alkyl, aryl and heteroaryl is optionally substituted with one or more suitable substituents. $R_1$, $R_2$, may be joined together with the nitrogen to form a 3- to 12-membered ring (e.g., morpholino or piperidinyl) wherein the 3- to 12-membered ring is optionally substituted with one or more suitable substituents.

In some embodiments, the heteroaromatic is selected from a monocyclic heteroaromatic, a bicyclic heteroaromatic, or a tricyclic heteroaromatic.

In various embodiments, the platinum compound of the present teachings can be selected from:

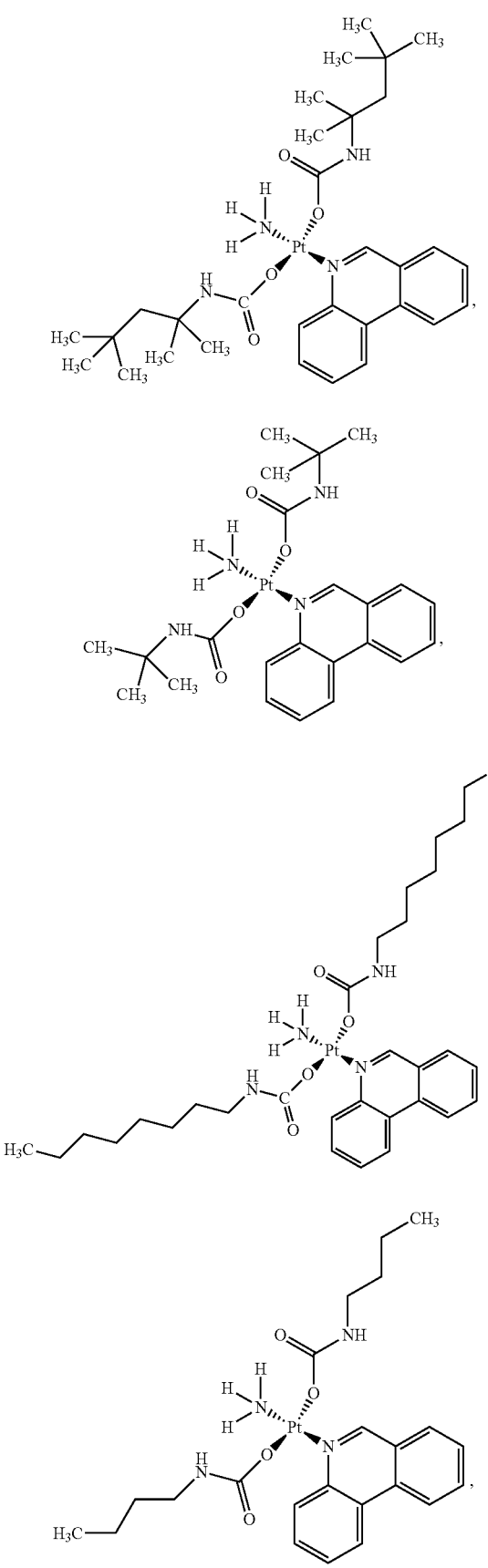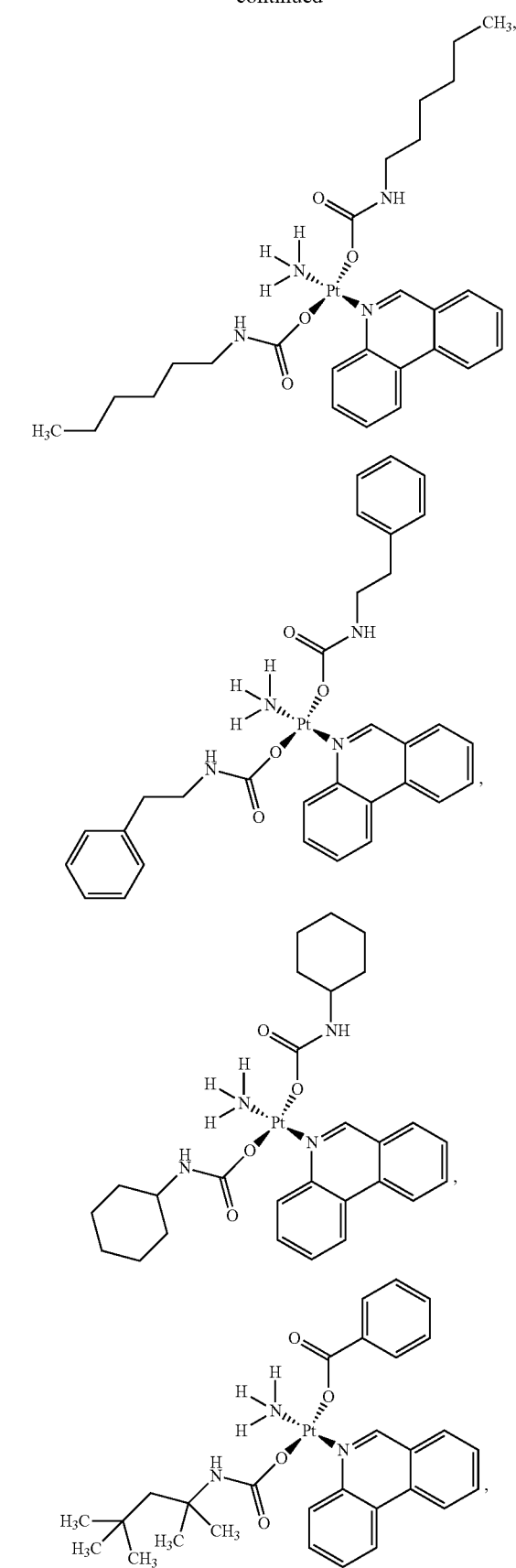

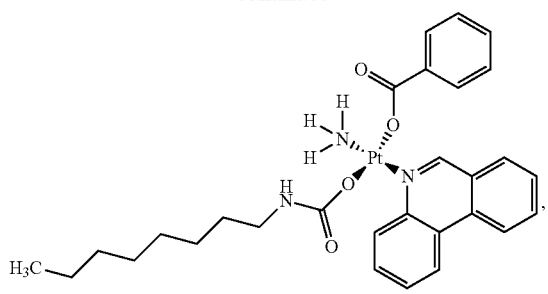

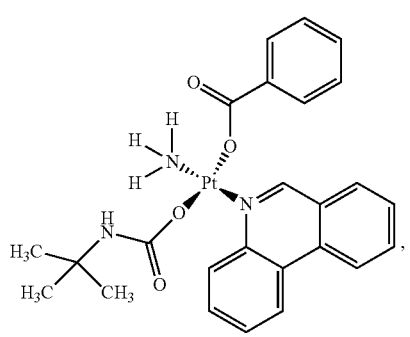

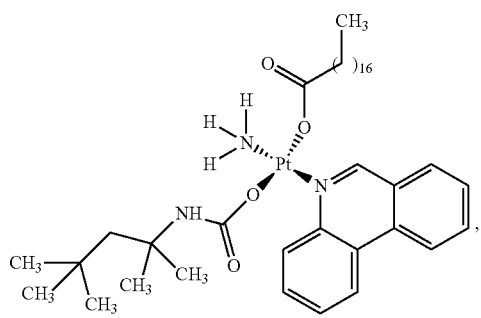

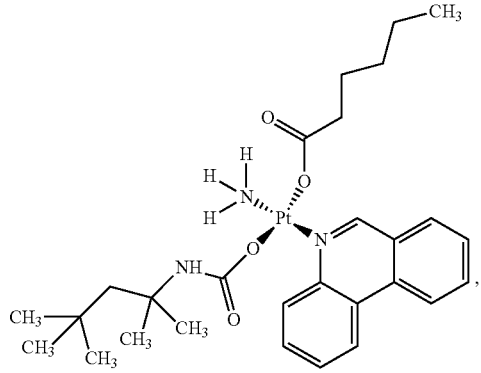

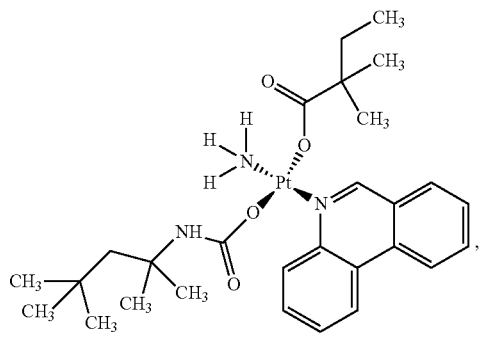

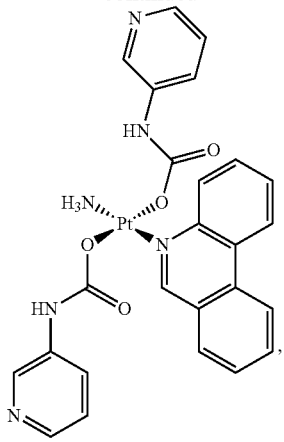

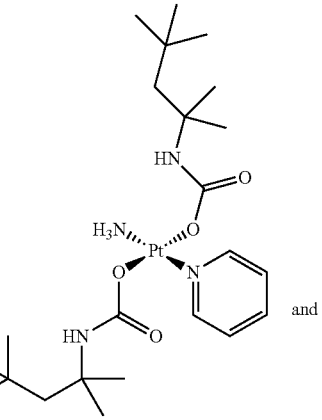

and

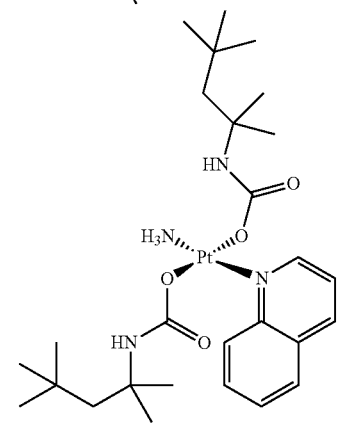

In another embodiment, the platinum complexes disclosed herein are encapsulated in, tethered to, or otherwise associated with a nanoparticle.

In other embodiments, the platinum compound(s) or complex(es) may be linked or conjugated to other active pharmaceutical agents.

In one embodiment, the disclosure includes a nanoparticle, comprising an inner portion and an outer surface, the inner portion comprising the platinum compound. In a further embodiment, the nanoparticles may contain a plurality of the same platinum compound, or may optionally contain a plurality of different platinum compounds.

As mentioned, the platinum compounds taught herein may be formulated as nanoparticles. In some embodiments they are encapsulated, in whole or in part, in the inner portion of the nanoparticles, or may be tethered or otherwise associated with nanoparticles. The nanoparticles may have a substantially spherical or non-spherical configuration (e.g., upon swelling or shrinkage). The nanoparticles may include polymer blends. In various embodiments, the base component of the nanoparticles comprises a polymer, a small molecule, or a mixture thereof. The base component can be biologically derived. For example, the small molecule can be a lipid. A "lipid," as used herein, refers to a hydrophobic or amphiphilic small molecule. Without attempting to limit the scope of the present teachings, lipids, because of their amphiphilicity, can form particles, including liposomes and micelles. The base component may be a cyclodextrin or an inorganic platform useful in forming nanoparticles.

In some embodiments, the base component comprises a polymer. For example, the polymer can be a biopolymer. Non-limiting examples include peptides or proteins (i.e., polymers of various amino acids), nucleic acids such as DNA or RNA. In certain embodiments, the polymer is amphiphilic, i.e., having a hydrophilic portion and a hydrophobic portion, or a relatively hydrophilic portion and a relatively hydrophobic portion.

In another embodiment, a pharmaceutical composition is provided comprising the nanoparticulate platinum compounds described herein, or pharmaceutically acceptable salts thereof, in a pharmaceutically acceptable vehicle. For example, an isotonic solution suitable for intravenous injection is contemplated by the present disclosure. In other embodiments, the compositions are formulated as oral, subcutaneous, and intramuscular dosage forms.

In yet another embodiment, the platinum compounds are released from the nanoparticle in a controlled fashion. Also contemplated are methods of making the nanoparticles, as well as methods for using them in the treatment or prevention of diseases or conditions.

In various embodiments, the methods of the present teachings are useful for the prevention or treatment of diseases that benefit from increased cell death or decreased cell proliferation. For example, the method of the present teachings can be used to increase cancer cell death or decrease cancer cell proliferation. The increased cancer cell death or decreased cancer proliferation can occur, for example, outside the body (in vitro) or inside the body (in vivo). Certain embodiments of the present teachings also provide for use of a compound as described herein in the manufacture of a medicament.

In some aspects, the invention relates to a method of inhibiting proliferation of a cell comprising contacting the cell with an effective amount of a compound as described herein, e.g., a platinum heterocycle compound. In some cases, the cell is a cancer cell.

Some embodiments include a method of inhibiting the rate of growth of a tumor, the size of a tumor or the volume of a tumor, the method comprising contacting the tumor with an effective amount of a compound as described herein, e.g., a platinum heterocycle compound.

In another aspect, the invention provides a method of delivering platinum to a tumor in a subject, the method comprising administering a compound, e.g., a platinum heterocycle, as described hereinto the subject.

In some aspects, the invention relates to a method of inhibiting proliferation of a cell comprising contacting the cell with an effective amount of a nanoparticle as described herein, e.g., a nanoparticle comprising a platinum heterocycle compound. In some cases, the cell is a cancer cell.

Some embodiments include a method of inhibiting the rate of growth of a tumor, the size of a tumor or the volume of a tumor, the method comprising contacting the tumor with an effective amount of a nanoparticle as described herein, e.g., a nanoparticle comprising a platinum heterocycle.

In another aspect, the invention provides a method of delivering platinum to a tumor in a subject, the method comprising administering a nanoparticle as described herein, e.g., a platinum heterocycle, to the subject.

Other embodiments, objects, features, and advantages will be set forth in the detailed description of the embodiments that follow and, in part, will be apparent from the description or may be learned by practice of the claimed invention. These objects and advantages will be realized and attained by the compositions and methods described and claimed herein. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

While the present disclosure is capable of being embodied in various forms, the description below of several embodiments is made with the understanding that the present disclosure is to be considered as an exemplification of the claimed subject matter, and is not intended to limit the appended claims to the specific embodiments illustrated and/or described. Accordingly, it should not be construed to limit the scope or breadth of the present invention. The headings used throughout this disclosure are provided for convenience only and are not to be construed to limit the claims in any way. Embodiments illustrated under any heading may be combined with embodiments illustrated under any other heading.

I. Definitions

For convenience, before further description of the present teachings, certain terms employed in the specification, examples, and appended claims are collected below. These definitions should be read in light of the remainder of the disclosure and understood as by a person of ordinary skill in the art. Unless defined otherwise, all technical and scientific terms used herein have the same meaning as commonly understood by a person of ordinary skill in the art.

The use of the terms "a," "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

The phrase "and/or," as used herein, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements).

As used herein, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein, the phrase "at least one" in reference to a list of one or more elements should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

As used herein, all transitional phrases such as "comprising," "including," "carrying," "having," "containing," "involving," "holding," "associated," "associated with" and the like are to be understood to be open-ended, i.e., to mean including but not limited to.

Only the transitional phrases "consisting of" and "consisting essentially of" shall be closed or semi-closed transitional phrases, respectively, as set forth in the United States Patent Office Manual of Patent Examining Procedures.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same or similar results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

The terms "therapeutic agent" or "active agent" or "pharmaceutically active agent" are art-recognized and refer to an agent capable of having a desired biological effect in a host.

The term "nanoparticle" as used herein refers to a particle having a characteristic dimension of less than about 1 micrometer, where the characteristic dimension of a particle is the diameter of a perfect sphere having the same volume as the particle. The plurality of particles can be characterized by an average diameter (e.g., the average diameter for the plurality of particles). In some embodiments, the diameter of the particles may have a Gaussian-type distribution. In some embodiments, the plurality of particles have an average diameter of less than about 300 nm, less than about 250 nm, less than about 200 nm, less than about 150 nm, less than about 100 nm, less than about 50 nm, less than about 30 nm, less than about 10 nm, less than about 3 nm, or less than about 1 nm. In some embodiments, the particles have an average diameter of at least about 5 nm, at least about 10 nm, at least about 30 nm, at least about 50 nm, at least about 100 nm, at least about 150 nm, or greater. In certain embodiments, the plurality of the particles have an average diameter of about 10 nm, about 25 nm, about 50 nm, about 100 nm, about 150 nm, about 200 nm, about 250 nm, about 300 nm, about 500 nm, or the like. In some embodiments, the plurality of particles have an average diameter between about 10 nm and about 500 nm, between about 50 nm and about 400 nm, between about 100 nm and about 300 nm, between about 150 nm and about 250 nm, between about 175 nm and about 225 nm, or the like. In some embodiments, the plurality of particles have an average diameter between about 10 nm and about 500 nm, between about 20 nm and about 400 nm, between about 30 nm and about 300 nm, between about 40 nm and about 200 nm, between about 50 nm and about 175 nm, between about 60 nm and about 150 nm, between about 70 nm and about 120 nm, or the like. For example, the average diameter can be between about 70 nm and 120 nm.

As used herein, a "subject" or a "patient" refers to any mammal (e.g., a human), such as a mammal that may be susceptible to a disease or disorder, for example, tumorigenesis or cancer. Examples include a human, a non-human primate, a cow, a horse, a pig, a sheep, a goat, a dog, a cat, or a rodent such as a mouse, a rat, a hamster, or a guinea pig.

In various embodiments, a subject refers to one that has been or will be the object of treatment, observation, or experiment. For example, a subject can be a subject diagnosed with cancer or otherwise known to have cancer or one selected for treatment, observation, or experiment on the basis of a known cancer in the subject.

As used herein, "treatment" or "treating" refers to an amelioration of a disease or disorder, or at least one discernible symptom thereof. In another embodiment, "treatment" or "treating" refers to an amelioration of at least one measurable physical parameter, not necessarily discernible by the patient. In yet another embodiment, "treatment" or "treating" refers to reducing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

As used herein, "prevention" or "preventing" refers to a reduction of the risk of acquiring a given disease or disorder.

The phrase "therapeutically effective amount" as used herein means that amount of a compound, material, or composition comprising a compound of the present teachings which is effective for producing some desired therapeutic effect. Accordingly, a therapeutically effective amount treats or prevents a disease or a disorder. In various embodiments, the disease or disorder is a cancer.

The term "therapeutic effect" is art-recognized and refers to a local or systemic effect in animals, e.g., mammals, including humans, caused by a pharmacologically active substance. The term thus means any substance intended for use in the diagnosis, cure, mitigation, treatment or prevention of disease or in the enhancement of desirable physical or mental development and conditions in an animal or human.

The term "modulation" is art-recognized and refers to up regulation (i.e., activation or stimulation), down regulation (i.e., inhibition or suppression) of a response, or the two in combination or apart.

The terms "systemic administration," "administered systemically," "peripheral administration" and "administered peripherally" are art-recognized and refer to the administration of a composition, therapeutic or other material other than directly into the central nervous system, such that it enters the patient's circulatory system and, thus, is subject to metabolism and other like processes, for example, intravenous or subcutaneous administration.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intra-articulare, subcapsular, subarachnoid, intraspinal, and intrasternal injection.

A dash ("-") that is not between two letters or symbols is used to indicate a point of attachment for a substituent. For example, —CONH$_2$ is attached through the carbon atom (C).

By "optional" or "optionally" is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those skilled in the art, with respect to any group containing one or more substituents, that such groups are not intended to introduce any substitution or substitution patterns that are sterically impractical, synthetically non-feasible, and/or inherently unstable.

The term "alkyl" as used herein refers to a saturated straight or branched hydrocarbon, such as a straight or branched group of 1-22, 1-8, 1-6, or 1-4 carbon atoms, referred to herein as ($C_1$-$C_{22}$)alkyl, ($C_1$-$C_5$)alkyl, ($C_1$-$C_6$) alkyl, and ($C_1$-$C_4$)alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

The term "alkenyl" as used herein refers to an unsaturated straight or branched hydrocarbon having at least one carbon-carbon double bond, such as a straight or branched group of 2-22, 2-8, 2-6, or 2-4 carbon atoms, referred to herein as ($C_2$-$C_{22}$)alkenyl, ($C_2$-$C_8$)alkenyl, ($C_2$-$C_6$)alkenyl, and ($C_2$-$C_4$)alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, and 4-(2-methyl-3-butene)-pentenyl.

The term "alkynyl" as used herein refers to an unsaturated straight or branched hydrocarbon having at least one carbon-carbon triple bond, such as a straight or branched group of 2-22, 2-8, 2-6, 2-4 carbon atoms, referred to herein as ($C_2$-$C_{22}$)alkynyl, ($C_2$-$C_8$)alkynyl, ($C_2$-$C_6$)alkynyl, and ($C_2$-$C_4$)alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl.

The term "cycloalkyl" as used herein refers to a saturated or unsaturated cyclic, bicyclic, other multicyclic, or bridged bicyclic hydrocarbon group. A cyclicalkyl group can have 3-22, 3-12, or 3-8 carbons, referred to herein as ($C_3$-$C_{22}$) cycloalkyl, ($C_3$-$C_{12}$)cycloalkyl, or ($C_3$-$C_8$)cycloalkyl, respectively. Exemplary cycloalkyl groups include, but are not limited to, cyclohexanes, cyclohexenes, cyclopentanes, and cyclopentenes. Cycloalkyl groups can be fused to other cycloalkyl saturated or unsaturated, aryl, or heterocyclyl groups.

Exemplary monocyclic cycloalkyl groups include, but are not limited to, cyclopentanes (cyclopentyls), cyclopentenes (cyclopentenyls), cyclohexanes (cyclohexyls), cyclohexenes (cyclopexenyls), cycloheptanes (cycloheptyls), cycloheptenes (cycloheptenyls), cyclooctanes (cyclooctyls), cyclooctenes (cyclooctenyls), cyclononanes (cyclononyls), cyclononenes (cyclononenyls), cyclodecanes (cyclodecyls), cyclodecenes (cyclodecenyls), cycloundecanes (cycloundecyls), cycloundecenes (cycloundecenyls), cyclododecanes (cyclododecyls), and cyclododecenes (cyclododecenyls). Other exemplary cycloalkyl groups, including bicyclic, multicyclic, and bridged cyclic groups, include, but are not limited to, bicyclobutanes (bicyclobutyls), bicyclopentanes (bicyclopentyls), bicyclohexanes (bicyclohexyls), bicycleheptanes (bicycloheptyls, including bicyclo[2,2,1]heptanes (bicycle[2,2,1]heptyls) and bicycle[3,2,0]heptanes (bicycle[3,2,0]heptyls)), bicyclooctanes (bicyclooctyls, including octahydropentalene (octahydropentalenyl), bicycle[3,2,1]octane (bicycle[3,2,1]octyl), and bicylo[2,2,2]octane (bicycle[2,2,2]octyl)), and adamantanes (adamantyls). Cycloalkyl groups can be fused to other cycloalkyl saturated or unsaturated, aryl, or heterocyclyl groups.

The term "aryl" as used herein refers to a mono-, bi-, or other multi-carbocyclic aromatic ring system. The aryl can have 6-22, 6-18, 6-14, or 6-10 carbons, referred to herein as ($C_6$-$C_{22}$)aryl, ($C_6$-$C_{18}$)aryl, ($C_6$-$C_{14}$)aryl, or ($C_6$-$C_{10}$)aryl, respectively. The aryl group can optionally be fused to one or more rings selected from aryls, cycloalkyls, and heterocyclyls. The term "bicyclic aryl" as used herein refers to an aryl group fused to another aromatic or non-aromatic carbocylic or heterocyclic ring. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl. Exemplary aryl groups also include, but are not limited to a monocyclic aromatic ring system, wherein the ring comprises 6 carbon atoms, referred to herein as "($C_6$)aryl" or phenyl. The phenyl group can also be fused to a cyclohexane or cyclopentane ring to form another aryl.

The term "arylalkyl" as used herein refers to an alkyl group having at least one aryl substituent (e.g., -aryl-alkyl-). Exemplary arylalkyl groups include, but are not limited to, arylalkyls having a monocyclic aromatic ring system, wherein the ring comprises 6 carbon atoms, referred to herein as "($C_6$)arylalkyl." The term "benzyl" as used herein refers to the group —$CH_2$-phenyl.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "heteroalkenyl" and "heteroalkynyl" refer to unsaturated aliphatic groups analogous in length and possible substitution to the heteroalkyls described above, but that contain at least one double or triple bond, respectively.

The term "heterocycle" refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. In some cases, the heterocycle may be 3- to 10-membered ring structures or 3- to 7-membered rings, whose ring structures include one to four heteroatoms. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycylic heterocycle. Thus, heterocycles also include bicyclic, tricyclic, and tetracyclic groups in which any of the above heterocyclic rings is fused to one or two rings independently selected from aryls, cycloalkyls, and heterocycles. The heterocycle may also be fused to a spirocyclic group.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine, oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like.

In some cases, the heterocycle may be bonded to a compound via a heteroatom ring atom (e.g., nitrogen). In some cases, the heterocycle may be bonded to a compound via a carbon ring atom. In some cases, the heterocycle is pyridine, imidazole, pyrazine, pyrimidine, pyridazine, acridine, acridin-9-amine, bipyridine, naphthyridine, quinoline, isoquinoline, benzoquinoline, benzoisoquinoline, phenanthridine-1,9-diamine, or the like.

The term "heteroaromatic" or "heteroaryl" as used herein refers to a mono-, bi-, or multi-cyclic aromatic ring system containing one or more heteroatoms, for example one to three heteroatoms, such as nitrogen, oxygen, and sulfur. Heteroaryls can also be fused to non-aromatic rings. In various embodiments, the term "heteroaromatic" or "heteroaryl," as used herein except where noted, represents a stable 5- to 7-membered monocyclic, stable 9- to 10-membered fused bicyclic, or stable 12- to 14-membered fused tricyclic heterocyclic ring system which contains an aromatic ring that contains at least one heteroatom selected from the group consisting of oxygen, nitrogen, and sulfur. In some embodiments, at least one nitrogen is in the aromatic ring.

Heteroaromatics or heteroaryls can include, but are not limited to, a monocyclic aromatic ring, wherein the ring comprises 2-5 carbon atoms and 1-3 heteroatoms, referred to herein as "($C_2$-$C_8$)heteroaryl." Illustrative examples of monocyclic heteroaromatic (or heteroaryl) include, but are not limited to, pyridine (pyridinyl), pyridazine (pyridazinyl), pyrimidine (pyrimidyl), pyrazine (pyrazyl), triazine (triazinyl), pyrrole (pyrrolyl), pyrazole (pyrazolyl), imidazole (imidazolyl), (1,2,3)- and (1,2,4)-triazole ((1,2,3)- and (1,2,4)-triazolyl), pyrazine (pyrazinyl), pyrimidine (pyrimidinyl), tetrazole (tetrazolyl), furan (furyl), thiophene (thienyl), isoxazole (isoxazolyl), thiazole (thiazolyl), isoxazole (isoxazolyl), and oxazole (oxazolyl). In certain embodiments, the heteroaromatics or heteroaryls is pyridine (pyridinyl) or imidazole (imidazolyl).

The term "bicyclic heteroaromatic" or "bicyclic heteroaryl" as used herein refers to a heteroaryl group fused to another aromatic or non-aromatic carbocylic or heterocyclic ring. Exemplary bicyclic heteroaromatics or heteroaryls include, but are not limited to 5,6- or 6,6-fused systems, wherein one or both rings contain heteroatoms. The term "bicyclic heteroaromatic" or "bicyclic heteroaryl" also encompasses reduced or partly reduced forms of fused aromatic system wherein one or both rings contain ring heteroatoms. The ring system may contain up to three heteroatoms, independently selected from oxygen, nitrogen, and sulfur.

Exemplary bicyclic heteroaromatics (or heteroaryls) include, but are not limited to, quinazoline (quinazolinyl), benzoxazole (benzoxazolyl), benzothiophene (benzothiophenyl), benzoxazole (benzoxazolyl), benzisoxazole (benzisoxazolyl), benzimidazole (benzimidazolyl), benzothiazole (benzothiazolyl), benzofurane (benzofuranyl), benzisothiazole (benzisothiazolyl), indole (indolyl), indazole (indazolyl), indolizine (indolizinyl), quinoline (quinolinyl), isoquinoline (isoquinolinyl), naphthyridine (naphthyridyl), phthalazine (phthalazinyl), phthalazine (phthalazinyl), pteridine (pteridinyl), purine (purinyl), benzotriazole (benzotriazolyl), and benzofurane (benzofuranyl). In some embodiments, the bicyclic heteroaromatic (or bicyclic heteroaryl) is selected from quinazoline (quinazolinyl), benzimidazole (benzimidazolyl), benzothiazole (benzothiazolyl), indole (indolyl), quinoline (quinolinyl), isoquinoline (isoquinolinyl), and phthalazine (phthalazinyl). In certain embodiments, the bicyclic heteroaromatic (or bicyclic heteroaryl) is quinoline (quinolinyl) or isoquinoline (isoquinolinyl). In certain embodiments, the bicyclic heteroaromatic (or bicyclic heteroaryl) is benzimidazole (benzimidazolyl).

The term "tricyclic heteroaromatic" or "tricyclic heteroaryl" as used herein refers to a bicyclic heteroaryl group fused to another aromatic or non-aromatic carbocyclic or heterocyclic ring. The term "tricyclic heteroaromatic" or "tricyclic heteroaryl" also encompasses reduced or partly reduced forms of fused aromatic system wherein one or both rings contain ring heteroatoms. Each of the ring in the tricyclic heteroaromatic (tricyclic heteroaryl) may contain up to three heteroatoms, independently selected from oxygen, nitrogen, and sulfur.

Exemplary tricyclic heteroaromatics (or heteroaryls) include, but are not limited to, acridine (acridinyl), 9H-pyrido[3,4-b]indole (9H-pyrido[3,4-b]indolyl), phenanthridine (phenanthridinyl), benzo[c][1,5]naphthyridine (benzo[c][1,5]naphthyridinyl), benzo[c][1,6]naphthyridine (benzo[c][1,6]naphthyridinyl), benzo[c][1,7]naphthyridine (benzo[c][1,7]naphthyridinyl), benzo[h][1,6]naphthyridine (benzo[h][1,6]naphthyridinyl), benzo[c][2,6]naphthyridine (benzo[c][2,6]naphthyridinyl), benzo[c][2,7]naphthyridine (benzo[c][2,7]naphthyridinyl), pyrido[1,2-a]benzimidazole (pyrido[1,2-a]benzimidazolyl), and pyrido[1,2-b]indazole (pyrido[1,2-b]indazolyl). In certain embodiments, the tricyclic heteroaromatics (or heteroaryls) is phenanthridine (phenanthridinyl), benzo[c][1,5]naphthyridine (benzo[c][1,5]naphthyridinyl), or pyrido[1,2-a]benzimidazole (pyrido[1,2-a]benzimidazolyl).

The term "alkoxy" as used herein refers to an alkyl group attached to an oxygen (—O— alkyl-). "Alkoxy" groups also include an alkenyl group attached to an oxygen ("alkenyloxy") or an alkynyl group attached to an oxygen ("alkynyloxy") groups. Exemplary alkoxy groups include, but are not limited to, groups with an alkyl, alkenyl or alkynyl group of 1-22, 1-8, or 1-6 carbon atoms, referred to herein as $(C_1$-$C_{22})$alkoxy, $(C_1$-$C_5)$alkoxy, or $(C_1$-$C_6)$alkoxy, respectively. Exemplary alkoxy groups include, but are not limited to, methoxy and ethoxy.

The term "cycloalkoxy" as used herein refers to a cycloalkyl group attached to an oxygen.

The term "aryloxy" or "aroxy" as used herein refers to an aryl group attached to an oxygen atom. Exemplary aryloxy groups include, but are not limited to, aryloxys having a monocyclic aromatic ring system, wherein the ring comprises 6 carbon atoms, referred to herein as "$(C_6)$aryloxy."

The term "amine" or "amino" as used herein refers to both unsubstituted and substituted amines, e.g., $NR_aR_bR_{b'}$, where $R_a$, $R_b$, and $R_{b'}$ are independently selected from alkyl, alkenyl, alkynyl, aryl, arylalkyl, carbamate, cycloalkyl, haloalkyl, heteroaryl, heterocyclyl, and hydrogen, and at least one of the $R_a$, $R_b$, and $R_{b'}$ is not hydrogen. The amine or amino can be attached to the parent molecular group through the nitrogen. The amine or amino also may be cyclic, for example any two of $R_a$, $R_b$, and $R_{b'}$ may be joined together and/or with the nitrogen to form a 3- to 12-membered ring (e.g., morpholino or piperidinyl). The term amino also includes the corresponding quaternary ammonium salt of any amino group. Exemplary amines include alkylamine, wherein at least one of $R_a$, $R_b$, or $R_{b'}$ is an alkyl group, or cycloalkylamine, wherein at least one of $R_a$, $R_b$, or $R_{b'}$ is a cycloalkyl group.

The term "ammonia" as used herein refers to $NH_3$.

The term "aldehyde" or "formyl" as used herein refers to —CHO.

The term "acyl" as used herein refers to a carbonyl radical attached to an alkyl, alkenyl, alkynyl, cycloalkyl, heterocycyl, aryl, or heteroaryl. Exemplary acyl groups include, but are not limited to, acetyl, formyl, propionyl, benzoyl, and the like.

The term "amide" as used herein refers to the form —NR$_c$C(O)(R$_d$)— or —C(O)NR$_c$R$_e$, wherein R$_c$, R$_d$, and R$_e$ are each independently selected from alkyl, alkenyl, alkynyl, aryl, arylalkyl, cycloalkyl, haloalkyl, heteroaryl, heterocyclyl, and hydrogen. The amide can be attached to another group through the carbon, the nitrogen, R$_c$, R$_d$, or R$_e$. The amide also may be cyclic, for example R$_c$ and R$_e$, may be joined to form a 3- to 12-membered ring, such as a 3- to 10-membered ring or a 5- or 6-membered ring. The term "amide" encompasses groups such as sulfonamide, urea, ureido, carbamate, carbamic acid, and cyclic versions thereof. The term "amide" also encompasses an amide group attached to a carboxy group, e.g., -amide-COOH or salts such as -amide-COONa.

The term "arylthio" as used herein refers to an aryl group attached to an sulfur atom. Exemplary arylthio groups include, but are not limited to, arylthios having a monocyclic aromatic ring system, wherein the ring comprises 6 carbon atoms, referred to herein as "$(C_6)$arylthio."

The term "arylsulfonyl" as used herein refers to an aryl group attached to a sulfonyl group, e.g., —S(O)$_2$-aryl-. Exemplary arylsulfonyl groups include, but are not limited to, arylsulfonyls having a monocyclic aromatic ring system, wherein the ring comprises 6 carbon atoms, referred to herein as "$(C_6)$arylsulfonyl."

The term "carbamate" as used herein refers to the form —R$_f$OC(O)N(R$_g$)—, —R$_f$OC(O)N(R$_g$)R$_h$—, or —OC(O)NR$_g$R$_h$, wherein R$_f$, R$_g$, and R$_h$ are each independently selected from alkyl, alkenyl, alkynyl, aryl, arylalkyl, cycloalkyl, haloalkyl, heteroaryl, heterocyclyl, and hydrogen. Exemplary carbamates include, but are not limited to, arylcarbamates or heteroaryl carbamates (e.g., wherein at least one of R$_f$, R$_g$ and R$_h$ are independently selected from aryl or heteroaryl, such as pyridinyl, pyridazinyl, pyrimidinyl, and pyrazinyl).

The term "carbonyl" as used herein refers to —C(O)—.

The term "carboxy" or "carboxylate" as used herein refers to R$_j$—COOH or its corresponding carboxylate salts (e.g., R$_j$—COONa), where R$_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. Exemplary carboxys include, but are not limited to, alkyl carboxy wherein R$_j$ is alkyl, such as —O—C(O)-alkyl. Exemplary carboxy also include aryl or heteoraryl carboxy, e.g., wherein R$_j$ is an aryl, such as phenyl and tolyl, or heteroaryl group such as pyridine, pyridazine, pyrmidine and pyrazine. The term carboxy also includes "carboxycarbonyl," e.g., a carboxy group attached to a carbonyl group, e.g., —C(O)—COOH or salts, such as —C(O)—COONa.

The term "dicarboxylic acid" as used herein refers to a group containing at least two carboxylic acid groups such as saturated and unsaturated hydrocarbon dicarboxylic acids and salts thereof. Exemplary dicarboxylic acids include alkyl dicarboxylic acids. Dicarboxylic acids include, but are not limited to succinic acid, glutaric acid, adipic acid, suberic acid, sebacic acid, azelaic acid, maleic acid, phthalic acid, aspartic acid, glutamic acid, malonic acid, fumaric acid, (+)/(−)-malic acid, (+)/(−) tartaric acid, isophthalic acid, and terephthalic acid. Dicarboxylic acids further include carboxylic acid derivatives thereof, such as anhydrides, imides, hydrazides (for example, succinic anhydride and succinimide).

The term "cyano" as used herein refers to —CN.

The term "ester" refers to the structure —C(O)O—, —C(O)O—$R_i$—, —$R_j$C(O)O—$R_i$—, or —$R_j$C(O)O—, where O is not bound to hydrogen, and $R_i$ and $R_j$ can independently be selected from alkoxy, aryloxy, alkyl, alkenyl, alkynyl, amide, amino, aryl, arylalkyl, cycloalkyl, ether, haloalkyl, heteroaryl, and heterocyclyl. $R_i$ can be a hydrogen, but $R_j$ cannot be hydrogen. The ester may be cyclic, for example the carbon atom and $R_j$, the oxygen atom and $R_i$, or $R_i$ and $R_j$ may be joined to form a 3- to 12-membered ring. Exemplary esters include, but are not limited to, alkyl esters wherein at least one of $R_i$ or $R_j$ is alkyl, such as —O—C(O)-alkyl, —C(O)—O-alkyl, and -alkyl-C(O)—O-alkyl-. Exemplary esters also include aryl or heteoraryl esters, e.g., wherein at least one of $R_i$ or $R_j$ is an aryl group, such as phenyl or tolyl, or a heteroaryl group, such as pyridine, pyridazine, pyrmidine, or pyrazine, such as a nicotinate ester. Exemplary esters also include reverse esters having the structure —$R_j$C(O)O—, where the oxygen is bound to the parent molecule. Exemplary reverse esters include succinate, D-argininate, L-argininate, L-lysinate, and D-lysinate. Esters also include carboxylic acid anhydrides and acid halides.

The term "ether" refers to the structure —$R_k$O—$R_l$—, where $R_k$ and $R_l$ can independently be alkyl, alkenyl, alkynyl, aryl, cycloalkyl, heterocyclyl, and ether. The ether can be attached to the parent molecular group through $R_k$ or $R_l$. Exemplary ethers include, but are not limited to, alkoxyalkyl and alkoxyaryl groups. Ethers also includes polyethers, e.g., where one or both of $R_k$ and $R_l$ are ethers.

The terms "halo" or "halogen" or "hal" as used herein refer to F, Cl, Br, or I.

The term "haloalkyl" as used herein refers to an alkyl group substituted with one or more halogen atoms. "Haloalkyls" also encompass alkenyl or alkynyl groups substituted with one or more halogen atoms.

The terms "hydroxy" and "hydroxyl" as used herein refers to —OH.

The term "hydroxyalkyl" as used herein refers to a hydroxy attached to an alkyl group.

The term "hydroxyaryl" as used herein refers to a hydroxy attached to an aryl group.

The term "ketone" as used herein refers to the structure —C(O)—$R_m$ (such as acetyl, —C(O)CH$_3$) or —$R_m$—C(O)—$R_n$—. The ketone can be attached to another group through $R_m$ or $R_n$. $R_m$ or $R_n$ can be alkyl, alkenyl, alkynyl, cycloalkyl, heterocyclyl or aryl, or $R_m$ or $R_n$ can be joined to form, for example, a 3- to 12-membered ring.

The term "monoester" as used herein refers to an analogue of a dicarboxylic acid wherein one of the carboxylic acids is functionalized as an ester and the other carboxylic acid is a free carboxylic acid or salt of a carboxylic acid. Examples of monoesters include, but are not limited to, to monoesters of succinic acid, glutaric acid, adipic acid, suberic acid, sebacic acid, azelaic acid, oxalic and maleic acid.

The term "nitro" as used herein refers to —NO$_2$.

The term "nitrate" as used herein refers to NO$_3^-$.

The term "perfluoroalkyl" as used herein refers to an alkyl group in which all of the hydrogen atoms have been replaced by fluorine atoms. Exemplary perfluroalkyl groups include, but are not limited to, $C_1$-$C_5$ perfluoroalkyl, such as trifluoromethyl.

The term "perfluorocycloalkyl" as used herein refers to a cycloalkyl group in which all of the hydrogen atoms have been replaced by fluorine atoms.

The term "perfluoroalkoxy" as used herein refers to an alkoxy group in which all of the hydrogen atoms have been replaced by fluorine atoms.

The term "phosphate" as used herein refers to the structure —OP(O)O$_2^{2-}$, —$R_o$OP(O)O$_2^{2-}$, —OP(O)(OR$_q$)O$^-$, or —$R_o$OP(O)(OR$_p$)O—, wherein $R_o$, $R_p$ and $R_q$ each independently can be alkyl, alkenyl, alkynyl, aryl, cycloalkyl, heterocyclyl, or hydrogen.

The term "sulfide" as used herein refers to the structure —$R_q$S—, where $R_q$ can be alkyl, alkenyl, alkynyl, aryl, arylalkyl, cycloalkyl, haloalkyl, heteroaryl, heterocyclyl. The sulfide may be cyclic, for example, forming a 3 to 12-membered ring. The term "alkylsulfide" as used herein refers to an alkyl group attached to a sulfur atom.

The term "sulfinyl" as used herein refers to the structure —S(O)O—, —$R_r$S(O)O—, —$R_r$S(O)OR$_s$—, or —S(O)OR$_s$—, wherein $R_r$ and $R_s$ can be alkyl, alkenyl, aryl, arylalkyl, cycloalkyl, haloalkyl, heteroaryl, heterocyclyl, hydroxyl. Exemplary sulfinyl groups include, but are not limited to, alkylsulfinyls wherein at least one of $R_r$ or $R_s$ is alkyl, alkenyl, or alkynyl.

The term "sulfonamide" as used herein refers to the structure —($R_t$)—N—S(O)$_2$—$R_v$— or —$R_t$($R_u$)N—S(O)$_2$—$R_v$, where $R_t$, $R_u$, and $R_v$ can be, for example, hydrogen, alkyl, alkenyl, alkynyl, aryl, cycloalkyl, and heterocyclyl. Exemplary sulfonamides include alkylsulfonamides (e.g., where $R_v$ is alkyl), arylsulfonamides (e.g., where $R_v$ is aryl), cycloalkyl sulfonamides (e.g., where $R_v$ is cycloalkyl), and heterocyclyl sulfonamides (e.g., where $R_v$ is heterocyclyl).

The term "sulfonate" as used herein refers to a salt or ester of a sulfonic acid. The term "sulfonic acid" refers to $R_w$SO$_3$H, where $R_w$ is alkyl, alkenyl, alkynyl, aryl, cycloalkyl, or heterocyclyl (e.g., alkylsulfonyl). The term "sulfonyl" as used herein refers to the structure $R_x$SO$_2$—, where $R_x$, can be alkyl, alkenyl, alkynyl, aryl, cycloalkyl, and heterocyclyl (e.g., alkylsulfonyl). The term "alkylsulfonyl" as used herein refers to an alkyl group attached to a sulfonyl group. "Alkylsulfonyl" groups can optionally contain alkenyl or alkynyl groups. In various embodiments, the sulfonate refers to $R_w$SO$_3^-$, where $R_w$ is alkyl, alkenyl, alkynyl, aryl, cycloalkyl, or heterocyclyl.

The term "sulfonate" as used herein refers $R_w$SO$_3^-$, where $R_w$ is alkyl, alkenyl, alkynyl, cycloalkyl, aryl, heterocyclyl, hydroxyl, alkoxy, aroxy, or aralkoxy, where each of the alkyl, alkenyl, alkynyl, cycloalkyl, aryl, heteroaryl, alkoxy, aroxy, or aralkoxy optionally is substituted. Non-limiting examples include triflate (also known as trifluoromethanesulfonate, CF$_3$SO$_3^-$), benzenesulfonate, tosylate (also known as toluenesulfonate), and the like.

The term "thioketone" refers to the structure —$R_y$—C(S)—$R_z$—. The ketone can be attached to another group through $R_y$ or $R_z$. $R_y$ or $R_z$ can be alkyl, alkenyl, alkynyl, cycloalkyl, heterocyclyl or aryl, or $R_y$ or $R_z$ can be joined to form a ring, for example, a 3- to 12-membered ring.

Each of the above groups may be optionally substituted. As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a functional group by which a molecule is identified, e.g., such that the "substituted" functional group becomes, through substitution, a different functional group. For example, a "substituted phenyl group" must still comprise the phenyl moiety and cannot be modified by substitution, in this definition, to become, e.g., a pyridine ring.

In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of the present teachings, the heteroatoms such as nitrogen may have hydrogen substituents and/or any permissible substituents of organic compounds described herein which satisfy the valencies of the heteroatoms.

In various embodiments, the substituent is selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone, each of which optionally is substituted with one or more suitable substituents. In some embodiments, the substituent is selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, thioketone, ester, heterocyclyl, —CN, aryl, aryloxy, perhaloalkoxy, aralkoxy, heteroaryl, heteroaryloxy, heteroarylalkyl, heteroaralkoxy, azido, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, cyano, alkoxyalkyl, perhaloalkyl, arylalkyloxyalkyl, and the like. In some embodiments, the substituent is selected from cyano, halogen, hydroxyl, and nitro.

As a non-limiting example, in various embodiments when one of the $R_a$, $R_b$, and $R_{b'}$ in $NR_aR_bR_{b'}$, referred to herein as an amine or amino, is selected from alkyl, alkenyl, alkynyl, cycloalkyl, and heterocyclyl, each of the alkyl, alkenyl, alkynyl, cycloalkyl, and heterocyclyl independently can be optionally substituted with one or more substituents each independently selected from alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone, wherein each of the alkoxy, aryloxy, alkyl, alkenyl, alkynyl, amide, amino, aryl, arylalkyl, carbamate, carboxy, cycloalkyl, ester, ether, formyl, haloalkyl, heteroaryl, heterocyclyl, ketone, phosphate, sulfide, sulfinyl, sulfonyl, sulfonic acid, sulfonamide, and thioketone can be further substituted with one or more suitable substituents. In some embodiments when the amine is an alkyl amine or a cycloalkylamine, the alkyl or the cycloalkyl can be substituted with one or more substituents each independently selected from alkoxy, aryloxy, alkyl, alkenyl, alkynyl, amide, amino, aryl, arylalkyl, carbamate, carboxy, cyano, cycloalkyl, ester, ether, formyl, halogen, haloalkyl, heteroaryl, heterocyclyl, hydroxyl, ketone, nitro, phosphate, sulfide, sulfinyl, sulfonyl, sulfonic acid, sulfonamide, and thioketone. In certain embodiments when the amine is an alkyl amine or a cycloalkylamine, the alkyl or the cycloalkyl can be substituted with one or more substituents each independently selected from amino, carboxy, cyano, and hydroxyl. For example, the alkyl or the cycloalkyl in the alkyl amine or the cycloalkylamine is substituted with an amino group, forming a diamine.

As used herein, a "suitable substituent" refers to a group that does not nullify the synthetic or pharmaceutical utility of the compounds of the invention or the intermediates useful for preparing them. Examples of suitable substituents include, but are not limited to: $(C_1-C_{22})$, $(C_1-C_8)$, $(C_1-C_6)$, or $(C_1-C_4)$ alkyl, alkenyl or alkynyl; $(C_6-C_{22})$, $(C_6-C_{18})$, $(C_6-C_{14})$, or $(C_6-C_{10})$ aryl; $(C_2-C_{21})$, $(C_2-C_{17})$, $(C_2-C_{13})$, or $(C_2-C_9)$ heteroaryl; $(C_3-C_{22})$, $(C_3-C_{12})$, or $(C_3-C_8)$ cycloalkyl; $(C_1-C_{22})$, $(C_1-C_8)$, $(C_1-C_6)$, or $(C_1-C_4)$ alkoxy; $(C_6-C_{22})$, $(C_6-C_{18})$, $(C_6-C_{14})$, or $(C_6-C_{10})$ aryloxy; —CN; —OH; oxo; halo, carboxy; amino, such as —NH($(C_1-C_{22})$, $(C_1-C_8)$, $(C_1-C_6)$ or $(C_1-C_4)$ alkyl), —N($(C_1-C_{22})$, $(C_1-C_8)$, $(C_1-C_6)$, or $(C_1-C_4)$ alkyl)$_2$, —NH($(C_6)$aryl), or —N($(C_6-C_{10})$ aryl)$_2$; formyl; ketones, such as —CO($(C_1-C_{22})$, $(C_1-C_8)$, $(C_1-C_6)$, or $(C_1-C_4)$ alkyl), —CO($(C_6-C_{10})$ aryl) esters, such as —CO$_2$($(C_1-C_{22})$, $(C_1-C_8)$, $(C_1-C_6)$, or $(C_1-C_4)$ alkyl) and —CO$_2$($(C_6-C_{10})$ aryl). One of skill in art can readily choose a suitable substituent based on the stability and pharmacological and synthetic activity of the compound of the invention.

Unless otherwise specified, the chemical groups include their corresponding monovalent, divalent, trivalent, and tetravalent groups. For example, methyl include monovalent methyl (—CH$_3$), divalent methyl (—CH$_2$—, methylyl), and trivalent methyl

and tetravalent methyl

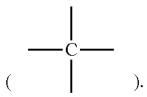

Unless otherwise specified, all numbers expressing quantities of ingredients, reaction conditions, and other properties or parameters used in the specification and claims are to be understood as being modified in all instances by the term "about." Accordingly, unless otherwise indicated, it should be understood that the numerical parameters set forth in the following specification and attached claims are approximations. At the very least, and not as an attempt to limit the application of the doctrine of equivalents to the scope of the claims, numerical parameters should be read in light of the number of reported significant digits and the application of ordinary rounding techniques.

All numerical ranges herein include all numerical values and ranges of all numerical values within the recited range of numerical values. As a non-limiting example, ($C_1$-$C_6$) alkyls also include any one of $C_1$, $C_2$, $C_3$, $C_4$, $C_5$, $C_6$, ($C_1$-$C_2$), ($C_1$-$C_3$), ($C_1$-$C_4$), ($C_1$-$C_5$), ($C_2$-$C_3$), ($C_2$-$C_4$), ($C_2$-$C_8$), ($C_2$-$C_6$), ($C_3$-$C_4$), ($C_3$-$C_5$), ($C_3$-$C_6$), ($C_4$-$C_5$), ($C_4$-$C_6$), and ($C_5$-$C_6$) alkyls.

Further, while the numerical ranges and parameters setting forth the broad scope of the disclosure are approximations as discussed above, the numerical values set forth in the Examples section are reported as precisely as possible. It should be understood, however, that such numerical values inherently contain certain errors resulting from the measurement equipment and/or measurement technique.

A "polymer," as used herein, is given its ordinary meaning as used in the art, i.e., a molecular structure comprising one or more repeating units (monomers), connected by covalent bonds. The repeating units may all be identical, or in some cases, there may be more than one type of repeating unit present within the polymer.

If more than one type of repeating unit is present within the polymer, then the polymer is said to be a "copolymer." It is to be understood that in any embodiment employing a polymer, the polymer being employed may be a copolymer in some cases. The repeating units forming the copolymer may be arranged in any fashion. For example, the repeating units may be arranged in a random order, in an alternating order, or as a "block" copolymer, i.e., comprising one or more regions each comprising a first repeating unit (e.g., a first block), and one or more regions each comprising a second repeating unit (e.g., a second block), etc. Block copolymers may have two (a diblock copolymer), three (a triblock copolymer), or more numbers of distinct blocks.

The term "hydrophilic," as used herein, generally describes the property of attracting water and the term "hydrophobic," as used herein, generally describes the property of repelling water. Thus, a hydrophilic compound (e.g., small molecule or polymer) is one generally that attracts water and a hydrophobic compound (e.g., small molecule or polymer) is one that generally repels water. A hydrophilic or a hydrophobic compound can be identified, for example, by preparing a sample of the compound and measuring its contact angle with water. In some cases, the hydrophilicity of two or more compounds may be measured relative to each other, i.e., a first compound may be more hydrophilic than a second compound.

The term "pharmaceutically acceptable counter ion" refers to a pharmaceutically acceptable anion or cation. In various embodiments, the pharmaceutical acceptable counter ion is a pharmaceutical acceptable ion. For example, the pharmaceutical acceptable counter ion is selected from citrate, matate, acetate, oxalate, chloride, bromide, iodide, nitrate, sulfate, bisulfate, phosphate, acid phosphate, isonicotinate, acetate, lactate, salicylate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)). In some embodiments, the pharmaceutical acceptable counter ion is selected from chloride, bromide, iodide, nitrate, sulfate, bisulfate, phosphate, acid phosphate, citrate, matate, acetate, oxalate, acetate, lactate, stearate and sodium bis(2-ethylhexyl) sulfosuccinate. In particular embodiments, the pharmaceutical acceptable counter ion is selected from chloride, bromide, iodide, nitrate, sulfate, bisulfate, and phosphate.

The term "pharmaceutically acceptable salt(s)" refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to sulfate, citrate, matate, acetate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions, that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

A pharmaceutically acceptable salt can be derived from an acid selected from 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid, aspartic acid, benzenesulfonic acid, benzoic acid, camphoric acid, camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid, gluconic acid, glucuronic acid, glutamic acid, glutaric acid, glycerophosphoric acid, glycolic acid, hippuric acid, hydrobromic acid, hydrochloric acid, isethionic, isobutyric acid, lactic acid, lactobionic acid, lauric acid, maleic acid, malic acid, malonic acid, mandelic acid, methanesulfonic acid, mucic, naphthalene-1,5-disulfonic acid, naphthalene-2-sulfonic acid, nicotinic acid, nitric acid, oleic acid, oxalic acid, palmitic acid, pamoic acid, pantothenic, phosphoric acid, proprionic acid, pyroglutamic acid, salicylic acid, sebacic acid, stearic acid, succinic acid, sulfuric acid, tartaric acid, thiocyanic acid, toluenesulfonic acid, trifluoroacetic, and undecylenic acid.

The term "bioavailable" is art-recognized and refers to a form of the subject invention that allows for it, or a portion of the amount administered, to be absorbed by, incorporated to, or otherwise physiologically available to a subject or patient to whom it is administered.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any supplement or composition, or component thereof, from one organ, or portion of the body, to another organ, or portion of the body. Each carrier must be "acceptable" in the sense of being compatible with the other ingredients of the formulation and not injurious to the patient.

II. Platinum Compounds

In various embodiments, the compounds of the present teachings include platinum compounds each having at least one heterocycle ligand. For example, the compound of the present teachings has Formula I:

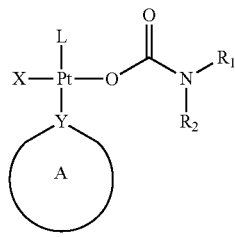

I wherein:
X is a halide, carboxylate, carbonate, carbamate, sulfonate, sulfate, or phosphate;
L each is an independently amine or an independently substituted amine;
Y is selected from Nitrogen, Oxygen, Phosphorus, and Sulfur;
A together with Y form a heteroaromatic optionally substituted with one or more substituents each independently selected from halogen, cyano, nitro, hydroxyl, ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide, wherein each of the ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide is optionally substituted with one or more suitable substituents; and wherein X and L form a bidentate ligand, or
A together with Y or X form a bidentate ligand.
$R_1$ and $R_2$ are each independently H, alkyl, aryl and heteroaryl wherein each of the H, alkyl, aryl and heteroaryl is optionally substituted with one or more suitable substituents. $R_1$, $R_2$, may be joined together with the nitrogen to form a 3- to 12-membered ring (e.g., morpholino or piperidinyl) wherein the 3- to 12-membered ring is optionally substituted with one or more suitable substituents.

In some embodiments, the heteroaromatic is selected from a monocyclic heteroaromatic, a bicyclic heteroaromatic, or a tricyclic heteroaromatic.

In some embodiments, X is —O(C=O)$R^a$ or is —O(C=O)—N—($R^a$)($R^b$); wherein $R^a$ and $R^b$ are hydrogen, alkyl, aryl, arylalkyl, or cycloalkyl, wherein each of the alkyl, aryl, arylalkyl, and cycloalkyl is optionally substituted with one or more suitable substituents. In some embodiments, X is formyl, acetate, propionate, butyrate, or benzoate, wherein each of the acetate, propionate, butyrate, and benzoate optionally is substituted with one or more suitable substituents (e.g., halogen, hydroxyl, alkoxy, aroxyl, ester, amino, alkyl, aryl, cycloalkyl, heteroaryl, or cycloheteroalkyl). For example, X is acetate or 4-cyclohexylbutyrate. In some embodiments, X is a sulfonate, phosphate, or sulfate. For example, X can be tosylate. In some embodiments, X is a halide.

In some embodiments, L is an amine or a substituted amine. In some embodiments, Y is N. In some embodiments, the heteroaromatic is selected from a monocyclic heteroaromatic, a bicyclic heteroaromatic, or a tricyclic heteroaromatic.

In one embodiment, the platinum compound of the present teachings is provided as follows:

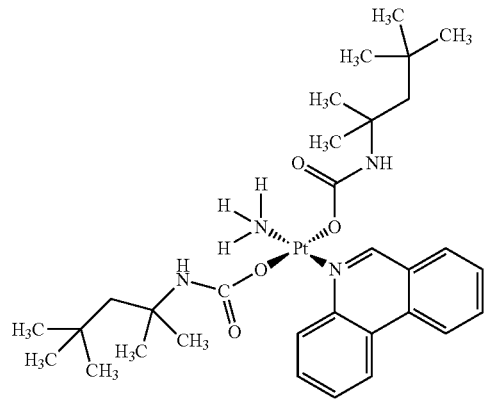

In another embodiment, the platinum compound of the present teachings is provided as follows:

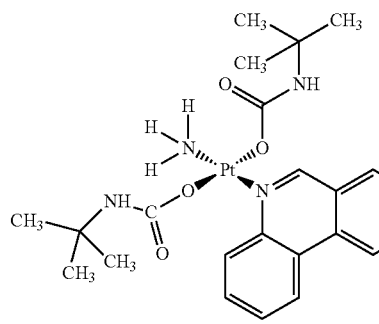

In yet another embodiment, the platinum compound of the present teachings is provided as follows:

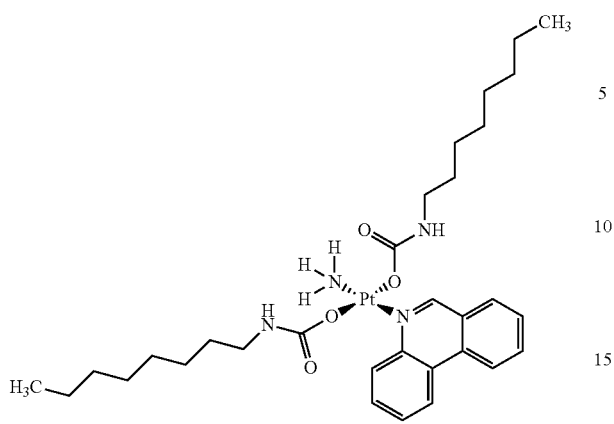

In yet another embodiment, the platinum compound of the present teachings is provided as follows:

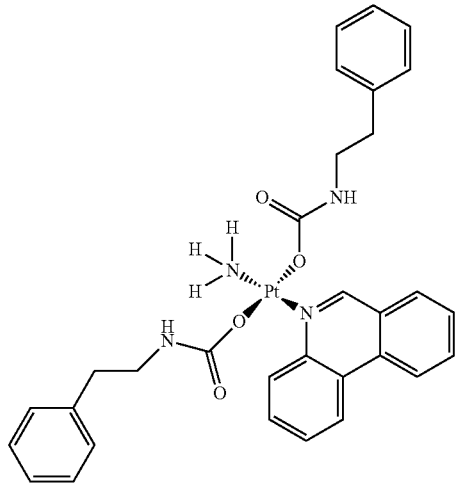

In another embodiment, the platinum compound of the present teachings is provided as follows:

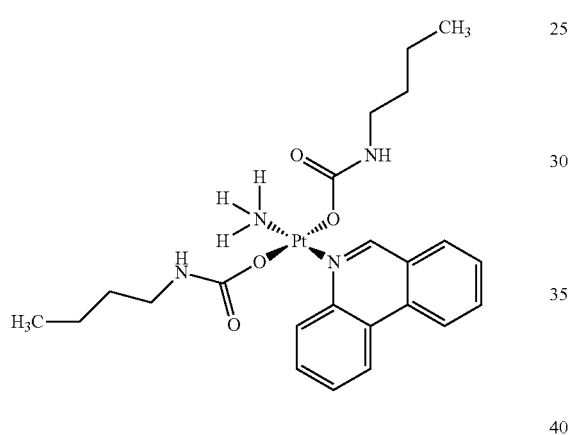

In another embodiment, the platinum compound of the present teachings is provided as follows:

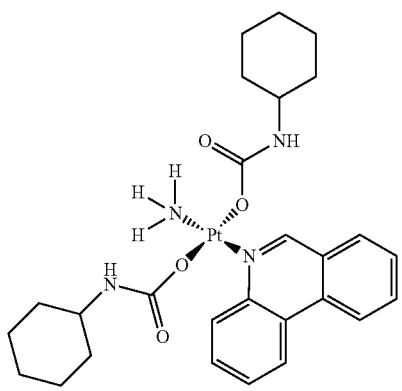

In yet another embodiment, the platinum compound of the present teachings is provided as follows:

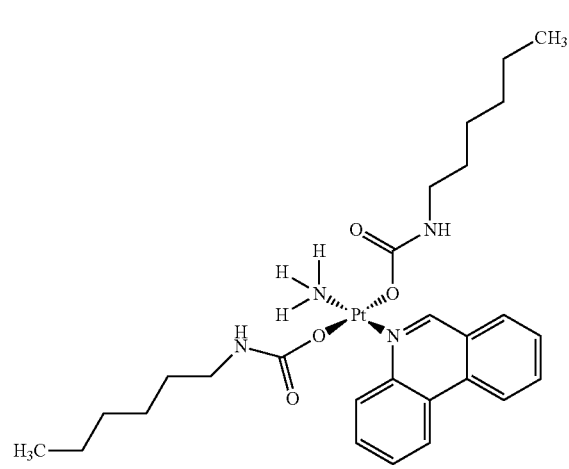

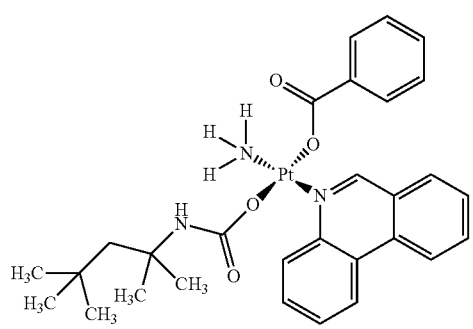

In yet another embodiment, the platinum compound of the present teachings is provided as follows:

In yet another embodiment, the platinum compound of the present teachings is provided as follows:

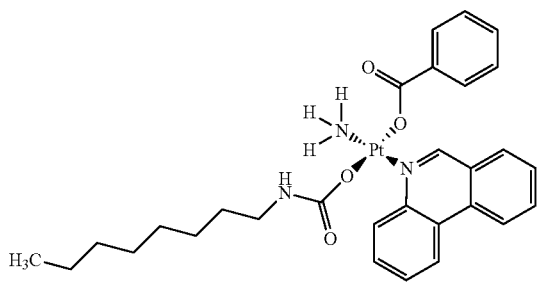

In yet another embodiment, the platinum compound of the present teachings is provided as follows:

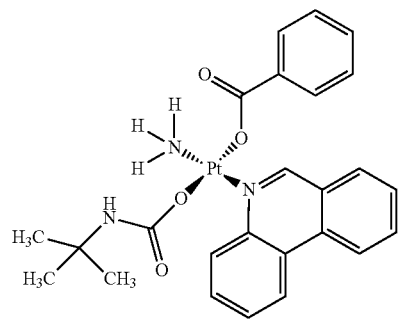

In another embodiment, the platinum compound of the present teachings is provided as follows:

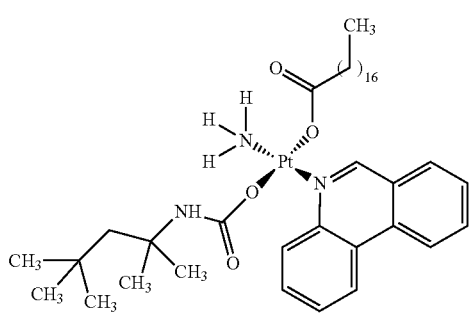

In one embodiment, the platinum compound of the present teachings is provided as follows:

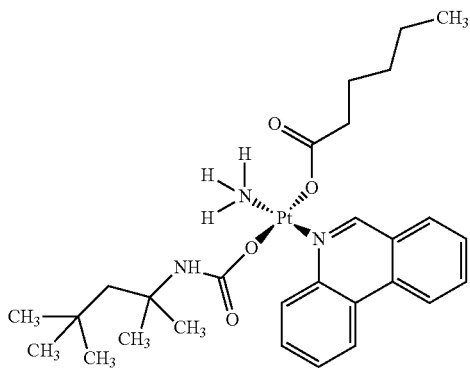

In another embodiment, the platinum compound of the present teachings is provided as follows:

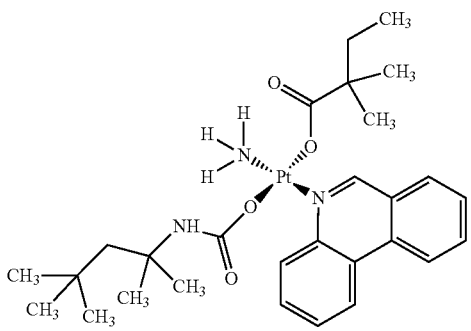

In yet another embodiment, the platinum compound of the present teachings is provided as follows:

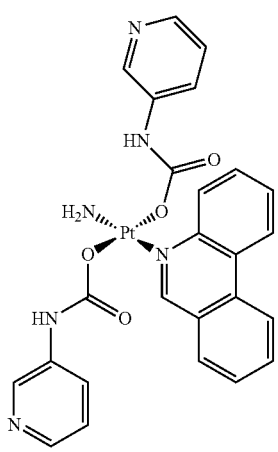

In yet another embodiment, the platinum compound of the present teachings is provided as follows:

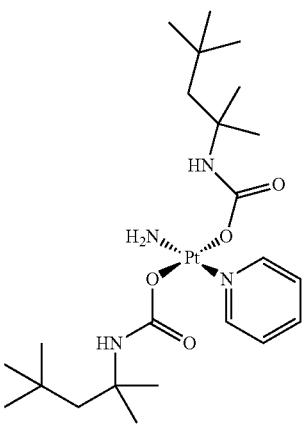

In yet another embodiment, the platinum compound of the present teachings is provided as follows:

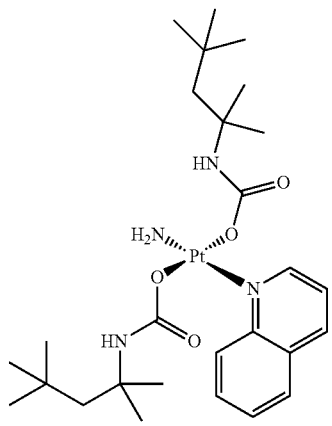

In some embodiments, the compound has Formula II:

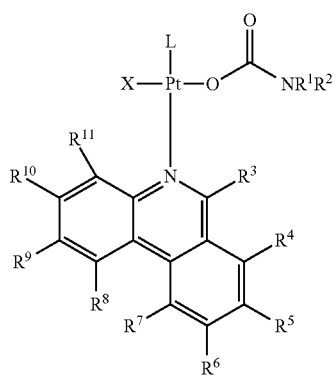

II wherein $R^3$, $R^4$, $R^5$, $R^6$, $R^7$, $R^8$, $R^9$, $R^{10}$, and $R^{11}$ each is independently selected from hydrogen, halogen, cyano, nitro, hydroxyl, ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide, wherein each of the ester, ether, alkoxy, aryloxy, amino, amide, carbamate, alkyl, alkenyl, alkynyl, aryl, arylalkyl, cycloalkyl, heteroaryl, heterocyclyl, phosphono, phosphate, sulfide, sulfinyl, sulfino, sulfonyl, sulfo, and sulfonamide is optionally substituted with one or more suitable substituents; or optionally, two adjacent substituents selected from $R^3$, $R^4$, $R^5$, $R^6$, $R^7$, $R^8$, $R^9$, $R^{10}$, and $R^{11}$ are connected to form an optionally substituted 5 or 6-membered ring; and L, X, and Z are as defined herein.

In some embodiments, $R^3$, $R^4$, $R^5$, $R^6$, $R^7$, $R^8$, $R^9$, $R^{10}$, and $R^{11}$ each is independently selected from hydrogen, halogen, cyano, nitro, hydroxyl, ester, ether, alkoxy, aryloxy, amino, amide, alkyl, aryl, cycloalkyl, and heteroaryl, wherein each of the ester, ether, alkoxy, aryloxy, amino, amide, alkyl, aryl, cycloalkyl, and heteroaryl is optionally substituted with one or more suitable substituents. For example, $R^3$, $R^4$, $R^5$, $R^6$, $R^7$, $R^8$, $R^9$, $R^{10}$, and $R^{11}$ each can be hydrogen, halogen, hydroxyl, alkoxy, amino, alkyl, or aryl, wherein each of the alkoxy, amino, alkyl, and aryl optionally is substituted with one or more suitable substituents.

In certain embodiments, $R^3$, $R^4$, $R^5$, $R^6$, $R^7$, $R^8$, $R^9$, $R^{10}$, and $R^{11}$ each is hydrogen, halogen, or alkyl optionally substituted with one or more suitable substituents. In other embodiments, $R^3$ is hydrogen, methyl, ethyl, propyl, isopropyl, or t-butyl. In some embodiments, $R^4$ is hydrogen. In some embodiment, $R^5$ is hydrogen, F, Cl, Br, methyl, ethyl, propyl, isopropyl, or t-butyl. In some embodiment, $R^8$ is hydrogen, F, Cl, Br, methyl, ethyl, propyl, isopropyl, or t-butyl. In some embodiments, $R^6$ is hydrogen. In some embodiments, $R^{11}$ is hydrogen.

In certain embodiments, $R^5$ is hydrogen, halogen, hydroxyl, alkoxy, alkyl, or aryl, wherein each of alkoxy, alkyl, and aryl optionally is substituted with one or more suitable substituents. In some embodiments, $R^5$ is hydrogen, F, Cl, Br, methyl, ethyl, propyl, isopropyl, t-butyl, hydroxyl, methoxy, ethoxy, propoxy, isopropoxy, t-butoxy, 2-methoxyethoxy, 2-ethoxyethoxy, —COOH, phenyl, or a substituted phenyl.

In certain embodiments, $R^9$ is hydrogen, halogen, alkyl, or aryl, wherein each of alkyl and aryl optionally is substituted with one or more suitable substituents. In some embodiments, $R^9$ is hydrogen, F, Cl, Br, methyl, ethyl, propyl, isopropyl, t-butyl, phenyl, or a substituted phenyl.

In certain embodiments, $R^{10}$ is hydrogen, amino, alkyl, or aryl, wherein each of amino, alkyl, and aryl optionally is substituted with one or more suitable substituents. In some embodiments, $R^{10}$ is hydrogen, F, Cl, Br, methylamino, ethylamino, propylamino, isopropylamino, t-butylamino, dimethylamino, diethylamino, diisopropylamino, methyl, ethyl, propyl, isopropyl, t-butyl, phenyl, or a substituted phenyl.

Some embodiments comprise compounds having two ligands (e.g., L and each of X) positioned in a cis configuration, i.e., the compound may be a cis isomer. However, it should be understood that compounds of the present teachings may also have two ligands (e.g., L and each of X) positioned in a trans configuration, i.e., the compound may be a trans isomer. Those of ordinary skill in the art would understand the meaning of these terms.

In some embodiments, any two ligands (e.g., L and each of X) may be joined together to form a bidentate or tridentate ligand, respectively. As will be known to those of ordinary skill in the art, a bidentate ligand, as used herein, when bound to a metal center, forms a metallacycle structure with the metal center, also known as a chelate ring. Bidentate ligands suitable for use in the present teachings include species that have at least two sites capable of binding to a metal center. For example, the bidentate ligand may comprise at least two heteroatoms that coordinate the metal center, or a heteroatom and an anionic carbon atom that coordinate the metal center. Examples of bidentate ligands suitable for use in the present teachings include, but are not limited to, alkyl and aryl derivatives of moieties such as amines, phosphines, phosphites, phosphates, imines, oximes, ethers, alcohols, thiolates, thioethers, hybrids thereof, substituted derivatives thereof, aryl groups (e.g., bis-aryl, heteroaryl-substituted aryl), heteroaryl groups, and the like. Specific examples of bidentate ligands include ethylenediamine, 2,2'-bipyridine, acetylacetonate, oxalate, and the like. Other non-limiting examples of bidentate ligands include diimines, pyridylimines, diamines, imineamines, iminethioether, iminephosphines, bisoxazoline, bisphosphineimines, diphosphines, phosphineamine, salen and other alkoxy imine ligands, amidoamines, imidothioether fragments and alkoxyamide fragments, and combinations of the above ligands.

The invention also comprises homologs, analogs, derivatives, enantiomers, diastereomers, tautomers, cis- and trans-isomers, and functionally equivalent compositions of compounds described herein. "Functionally equivalent" generally refers to a composition capable of treatment of patients having a disease (e.g., cancer) or of patients susceptible to a disease. It will be understood that the skilled artisan will be able to manipulate the conditions in a manner to prepare such homologs, analogs, derivatives, enantiomers, diastereomers, tautomers, cis- and trans-isomers, and functionally equivalent compositions. Homologs, analogs, derivatives, enantiomers, diastereomers, tautomers, cis- and trans-isomers, and functionally equivalent compositions which are about as effective or more effective than the parent compound are also intended for use in the method of the invention. Such compositions may also be screened by the assays described herein for increased potency and specificity towards a disease (e.g., cancer), generally with limited side effects. Synthesis of such compositions may be accomplished through typical chemical modification methods such as those routinely practiced in the art. Another aspect of the present invention provides any of the above-mentioned compounds as being useful for the treatment of a disease (e.g., cancer).

The compounds of the present teachings may be synthesized according to methods known in the art, including various methods described herein. For example, the method may comprise the reaction of cisplatin with one or more ligand sources.

In general, the compounds disclosed herein may be prepared by the methods illustrated in the general reaction schema described below, or by modifications thereof, using readily available starting materials, reagents and conventional synthesis procedures. In these reactions, it is also possible to make use of variants which are in themselves known, but are not mentioned here.

In another embodiment, the nanoparticle comprises an inner portion and an outer surface, and the inner portion comprising a platinum compound Some chemical bonds, such as hydrazone, ester, and amide bonds are sensitive to acidic pH values, for example, of the intracellular environment of tumor cells. At acidic pH, hydrogen ions catalyze the hydrolysis of these bonds which in turn releases the drug from its conjugate format. In the reducing environment of the cytoplasm of tumor cells some functional groups such as Pt(IV) complexes can be reduced to active Pt(II) complexes. Therefore, different pharmaceutically active agents, such as but not limited to cabazitaxel, platinum(IV) complexes, oxaliplatin, cisplatin, carboplatin, paclitaxel, docetaxel and the like having —OH, —$NH_2$, —SH, —COOH, alkenyl, phosphate, sulfate, heterocyclic NH, alkyne and/or ketonic groups, may be covalently linked together with a suitable spacer with alkyl chains of variable lengths.

Once formed, the platinum complex may be formulated into nanoparticles for delivery to a patient as described further below. In one embodiment, the platinum compounds disclosed herein are encapsulated in, tethered to or otherwise associated with a nanoparticle. The platinum complexes may be delivered alone or in combination with the conjugates described herein. The compounds of the present teachings may be synthesized according to methods known in the art, including various methods described herein. The present teachings therefore comprise compositions (including pharmaceutical compositions) comprising one or more of the compounds as described herein. In various embodiments, a composition of the present teachings comprises a particle and a conjugate described herein. In some embodiments, as described further in the sections below, the particle comprises a base component forming an inner portion and an exterior portion. In certain embodiments, the interior of the particle is more hydrophobic than the exterior of the particle. In certain other embodiments, the interior is more hydrophilic than the exterior.

The present teachings include platinum compounds, including nanoparticles thereof, pharmaceutical compositions, methods of producing such compositions and methods of using the same. In other aspects, the teachings provide methods for preparing drug delivery compositions, e.g., nanoparticles, such as polymers having pendant functional groups. One advantage of the present disclosure is that by engineering and blending distinct drug-functionalized and ligand-functionalized polymers, particles capable of delivering two, three, or more drugs can be reproducibly engineered and characterized. Additionally, these methods allow for characteristics of drug release and pharmacokinetics to be tuned for each type of agent and regardless of the characteristics of the active agents (i.e., solubility, charge, molecular weight, half-life, and/or biodistribution profiles). Further, by targeting drug-loaded particles to specific tissues or cells, e.g., cancer cells, synergistic drug effects can be achieved that can alter the biodistribution of active agents. This can translate to better efficacy and tolerability, making active agents suitable for potential clinical development.

III. Formulation of Nanoparticles

The platinum compounds taught herein may be formulated as nanoparticles. In some embodiments they are encapsulated, in whole or in part, in the inner portion of the nanoparticles, or tethered to or otherwise associated with the nanoparticles. The nanoparticles may have a substantially spherical or non-spherical configuration (e.g., upon swelling or shrinkage). The nanoparticles may include polymer blends. In various embodiments, the base component of the nanoparticles comprises a polymer, a small molecule, or a mixture thereof. The base component can be biologically derived. For example, the small molecule can be, for example, a lipid. A "lipid," as used herein, refers to a hydrophobic or amphiphilic small molecule. Without attempting to limit the scope of the present teachings, lipids, because of their amphiphilicity, can form particles, including liposomes and micelles.

In some embodiments, the base component comprises a polymer. For example, the polymer can be a biopolymer. Non-limiting examples include peptides or proteins (i.e., polymers of various amino acids), nucleic acids such as DNA or RNA. In certain embodiments, the polymer is amphiphilic, i.e., having a hydrophilic portion and a hydrophobic portion, or a relatively hydrophilic portion and a relatively hydrophobic portion.

In various embodiments, the base component is biocompatible, i.e., it does not typically induce an adverse response when inserted or injected into a subject. The adverse response can include significant inflammation and/or acute rejection of the polymer by the immune system, for instance, via a T-cell response. It will be recognized, of course, that "biocompatibility" is a relative term, and some degree of immune response is to be expected even for polymers that are highly compatible with living tissue. However, as used herein, "biocompatibility" refers to the acute rejection of material by at least a portion of the immune system, i.e., a non-biocompatible material implanted into a subject provokes an immune response in the subject that is severe enough such that the rejection of the material by the immune system cannot be adequately controlled, and is often of a degree such that the material must be removed from the subject.

Non-limiting examples of biocompatible polymers that may be useful in various embodiments of the present invention include polydioxanone (PDO), polyhydroxyalkanoate, polyhydroxybutyrate, poly(glycerol sebacate), polyglycolide, polylactide, polycaprolactone, or copolymers or derivatives including these and/or other polymers. In other embodiments, the base component may comprise liposomes, cyclodextrins or inorganic platforms as known generally in the art.

In various embodiments, the base component is biodegradable, i.e., the polymer is able to degrade, chemically and/or biologically, within a physiological environment, such as within the body. For instance, the polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer is degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

Examples of biodegradable polymers include, but are not limited to, poly(lactide) (or poly(lactic acid)), poly(glycolide) (or poly(glycolic acid)), poly(orthoesters), poly(caprolactones), polylysine, poly(ethylene imine), poly(acrylic acid), poly(urethanes), poly(anhydrides), poly(esters), poly(trimethylene carbonate), poly(ethyleneimine), poly(acrylic acid), poly(urethane), poly(beta amino esters) or the like, and copolymers or derivatives of these and/or other polymers, for example, poly(lactide-co-glycolide) (PLGA).

In various embodiments, the base component comprises polylactide or poly(lactic acid). In various embodiments, the base component comprises poly(glycolide). In various embodiments, the base component comprises poly(lactide-co-glycolide).

A person with ordinary skill in the art can choose polylactide, polyglycolide, or poly(lactide-co-glycolide) of different molecular weights according to various applications. In some embodiments, the polylactide, polyglycolide, or poly(lactide-co-glycolide) has a number average molecular weight of about 5 kDa to about 250 kDa. For example, the polylactide, polyglycolide, or poly(lactide-co-glycolide) has a number average molecular weight of about 5 kDa to about 150 kDa. In certain embodiments, the polylactide, polyglycolide, or poly(lactide-co-glycolide) has a number average molecular weight of about 5 kDa to about 10 kDa, about 10 kDa to about 20 kDa, about 20 kDa to about 30 kDa, about 30 kDa to about 40 kDa, about 40 kDa to about 50 kDa, about 50 kDa to about 60 kDa, about 60 kDa to about 70 kDa, about 70 kDa to about 80 kDa, about 80 kDa to about 90 kDa, about 90 kDa to about 100 kDa, about 100 kDa to about 110 kDa, about 110 kDa to about 120 kDa, about 120 kDa to about 130 kDa, about 130 kDa to about 140 kDa, or about 140 kDa to about 150 kDa. In certain embodiments, the polylactide, polyglycolide, or poly(lactide-co-glycolide) has a number average molecular weight of about 10 kDa to about 150 kDa, about 20 kDa to about 125 kDa, about 30 kDa to about 110 kDa, about 40 kDa to about 90 kDa, or about 50 kDa to about 80 kDa. For example, the polylactide, polyglycolide, or poly(lactide-co-glycolide) can have a number average molecular weight of about 15 kDa, about 35 kDa, about 50 kDa, about 60 kDa, about 80 kDa, about 90 kDa, about 100 kDa, or about 110 kDa. In particular embodiments, the polylactide, polyglycolide, or poly(lactide-co-glycolide) has a number average molecular weight of about 15 kDa.

In various embodiments, the base component has the capability of controlling immunogenicity. Nonexclusive examples of a polymeric base component include a poly(alkylene glycol) (also known as poly(alkylene oxide)), such as poly(propylene glycol), or poly(ethylene oxide), also known as poly(ethylene glycol) ("PEG"), having the formula —$(CH_2$—$CH_2$—$O)_n$—, where n is any positive integer. The poly(ethylene glycol) units may be present within the polymeric base component in any suitable form. For instance, the polymeric base component may be a block copolymer where one of the blocks is poly(ethylene glycol). A polymer comprising poly(ethylene glycol) repeating units is also referred to as a "PEGylated" polymer. Such polymers can control inflammation and/or immunogenicity (i.e., the ability to provoke an immune response), due to the presence of the poly(ethylene glycol) groups.

PEGylation may also be used, in some cases, to decrease charge interaction between a polymer and a biological moiety, e.g., by creating a hydrophilic layer on the surface of the polymer, which may shield the polymer from interacting with the biological moiety. For example, PEGylation may be used to create particles which comprise an interior which is more hydrophobic than the exterior of the particles. In some cases, the addition of poly(ethylene glycol) repeating units may increase plasma half-life of the polymeric conjugate, for instance, by decreasing the uptake of the polymer by the phagocytic system while decreasing transfection/uptake efficiency by cells.

In various embodiments, the PEG unit has a number average molecular weight of about 1 kDa to about 20 kDa. For example, the PEG unit can have a number average molecular weight of about 1 kDa to about 2 kDa, about 2 kDa to about 3 kDa, about 3 kDa to about 4 kDa, about 4 kDa to about 5 kDa, about 5 kDa to about 6 kDa, about 6 kDa to about 7 kDa, about 7 kDa to about 8 kDa, about 8 kDa to about 9 kDa, about 9 kDa to about 10 kDa, about 10 kDa to about 12 kDa, about 12 kDa to about 14 kDa, about 14 kDa to about 16 kDa, about 16 kDa to about 18 kDa, or about 18 kDa to about 20 kDa. In some embodiments, the PEG unit has a number average molecular weight of about 1 kDa to about 10 kDa. In certain embodiments, the PEG unit has a number average molecular weight of about 2 kDa to about 8 kDa, or about 3 kDa to about 7 kDa, or about 4 kDa to about 6 kDa. For example, the PEG unit has a number average molecular weight of about 2 kDa to about 6 kDa or about 3 kDa to about 5 kDa. In particular embodiments, the PEG unit has a number average molecular weight of about 3 KDa, 4 kDa, 5 kDa, or 6 kDa.

In various embodiments, the base component comprises a polylactide, a polyglycolide, or poly(lactide-co-glycolide) and a PEGylated polylactide, a PEGylated polyglycolide, or a PEGylated poly(lactide-co-glycolide). The weight percentage of the PEGylated polymer in the base component can be from 0% to 100%, including about 5% to about 95%, about 10% to about 90%, about 20% to about 80%, about 30% to about 70%, or about 40% to about 60%. In some embodiments, the weight percentage of the PEGylated polymer in the base component is about 30% to about 95% or about 40% to about 90%. In particular embodiments, the weight percentage of the PEGylated polymer in the base component is about 40%, 50%, 60%, 70%, 80%, 90%, or 100%. For example, the weight percentage of the PEGylated polymer in the base component is about 60%.

Those of ordinary skill in the art will know of methods and techniques for PEGylating a polymer, for example, by using EDC (1-ethyl-3-(3-dimethylaminopropyl) carbodiimide hydrochloride) and NHS (N-hydroxysuccinimide) to react a polymer to a PEG group terminating in an amine, for example, by ring opening polymerization techniques, or the like. In addition, certain embodiments are directed towards copolymers containing poly(ester-ether)s, e.g., polymers having repeating units joined by ester bonds (e.g., R—C(O)—O—R' bonds) and ether bonds (e.g., R—O—R' bonds).

In various embodiments, the particle comprises one or more compounds of the present teachings. In some embodiments, at least one of the compounds is contained within a particle of the present teachings. The term "contained within" may mean "located in a cavity of," "entirely embedded in," or "partially embedded in." For example, at least one of the compounds can be located in a cavity formed in a particle of the present teachings or otherwise embedded in a particle of the present teachings. In certain embodiments, at least one of the compounds is located in the cavity of a particle. In certain embodiments, at least one of the compounds is entirely embedded in a particle. In certain embodiments, at least one of the compounds is partially embedded in a particle.

In various embodiments, a substantial amount of at least one of the compounds is contained within particles of the present teachings. In some embodiments, about 90% or greater, about 80% or greater, about 70% or greater, or about 60% or greater of the total amount of at least one of the compounds included in the particles is contained within the particles. In certain embodiments, about 80% or greater of the total amount of at least one of the compounds included in the particles is contained within the particles. In certain embodiments, about 90% or greater of the total amount of at least one of the compounds included in the particles is contained within the particles. In certain embodiments, about 95% or greater of the total amount of at least one of the compounds included in the particles is contained within the particles.

In various embodiments, about 50% and greater, about 40% or greater, about 30% or greater, about 20% or greater, or about 10% or greater of the total amount of at least one of the compounds included in particles of the present teachings is contained within the particles. In some embodiments, about 10% or greater of the total amount of at least one of the compounds included in the particles is contained within the particles. In some embodiments, about 20% or greater of the total amount of at least one of the compounds included in the particles is contained within the particles. In some embodiments, about 30% or greater of the total amount of at least one of the compounds included in the particles is contained within the particles. In some embodiments, about 40% or greater of the total amount of at least one of the compounds included in the particles is contained within the particles. In some embodiments, about 50% or greater of the total amount of at least one of the compounds included in the particles is contained within the particles.

In various embodiments, the ratio of the compound to the base component in a solution prior to formation of a plurality of particles may affect the percent loading of the compound in the particle and/or the mean size of the particle. For example, an increase in the percent weight of the compound to the percent weight of the base component may increase the percent loading of the compound within the particle.

In some embodiments, the percent weight of the compound provided in a mixture comprising the compound and the base component is at least about 5%, at least about 10%, at least about 20%, at least about 30%, at least about 40%, at least about 50%, at least about 60%, at least about 70%, at least about 80%, at least about 90%, or at least about 100%. In certain embodiments, the percent weight is between about 5% and about 90%, between about 10% and about 80%, between about 10% and about 50%, between about 50% and about 90%, or any range therein. In particular embodiments, the weight percentage is about 5% to about 30% or about 5% to about 20%. For example, the weight percentage can be about 10%.

In some embodiments, the total percent loading of the compound in the plurality of particles is greater than about 0.01%, greater than about 0.05%, greater than about 0.1%, greater than about 0.5%, greater than about 1%, greater than about 2%, greater than about 5%, greater than about 10%, greater than about 15%, greater than about 20%, greater than about 25%, greater than about 30%, greater than about 35%, greater than about 40%, greater than about 45%, greater than about 50%, greater than about 55%, or greater. In some embodiments, the percent loading is between about 0.01% and about 50%, between about 0.05% and about 30%, between about 0.1% and about 50%, between about 0.05% and about 10%, between about 0.1% and about 10%, between about 1% and about 10%, or any range therein. In certain embodiments, the percentage loading is about 2%, about 3%, about 4%, about 5%, about 6%, about 7%, or about 8%. In particular embodiments, the percentage loading is about 5%, about 6%, about 7%, about 8%, about 9%, or about 10%.

Without wishing to be bound by theory, the size of a particle may alter the delivery (e.g., loss of payload, drug efflux, aggregations, delivery to desired location, etc.) of a compound of the present teachings from the particles. The size of the particles used in a delivery system may be selected based on the application, and will be readily known to those of ordinary skill in the art. For example, particles of smaller size (e.g., <200 nm) may be selected if systematic delivery of the particles throughout a patient's bloodstream is desired. As another example, particles of larger size (e.g., >200 nm) may be selected if sequestering of the particles by a patient's reticuloendothelial system upon injection is desired (e.g., sequestering of the particles in the liver, spleen, etc.). The desired length of time of delivery may also be considered when selecting particle size. For example, smaller particles may circulate in the blood stream for longer periods of time than larger particles.

In some embodiments, the particles may substantially accumulate at the site of a tumor. Without attempting to limit the scope of the present teaching, the accumulation may be due, at least in part, to the presence of a targeting moiety associated with the particle, as described herein; or, at least in part, due to an enhanced permeability and retention (EPR) effect, which allows for particles to accumulate specifically at a tumor site. The EPR effect will be known to those of ordinary skill in the art and refers to the property by which certain sizes of material (e.g., particles) tend to accumulate in tumor tissue much more than they do in normal tissues.

In various embodiments, a particle may be a nanoparticle, i.e., the particle has a characteristic dimension of less than about 1 micrometer, where the characteristic dimension of a particle is the diameter of a perfect sphere having the same volume as the particle. The plurality of particles can be characterized by an average diameter (e.g., the average diameter for the plurality of particles). In some embodiments, the diameter of the particles may have a Gaussian-type distribution. In some embodiments, the plurality of particles have an average diameter of less than about 300 nm, less than about 250 nm, less than about 200 nm, less than about 150 nm, less than about 100 nm, less than about 50 nm, less than about 30 nm, less than about 10 nm, less than about 3 nm, or less than about 1 nm. In some embodiments, the particles have an average diameter of at least about 5 nm, at least about 10 nm, at least about 30 nm, at least about 50 nm, at least about 100 nm, at least about 150 nm, or greater. In certain embodiments, the plurality of the particles have an average diameter of about 10 nm, about 25 nm, about 50 nm, about 100 nm, about 150 nm, about 200 nm, about 250 nm, about 300 nm, about 500 nm, or the like. In some embodiments, the plurality of particles have an average diameter between about 10 nm and about 500 nm, between about 50 nm and about 400 nm, between about 100 nm and about 300 nm, between about 150 nm and about 250 nm, between about 175 nm and about 225 nm, or the like. In some embodiments, the plurality of particles have an average diameter between about 10 nm and about 500 nm, between about 20 nm and about 400 nm, between about 30 nm and about 300 nm, between about 40 nm and about 200 nm, between about 50 nm and about 175 nm, between about 60 nm and about 150 nm, between about 70 nm and about 120 nm, or the like. For example, the average diameter can be between about 70 nm and 120 nm.

Another aspect of the present teachings relates to systems and methods of making the disclosed particles, including nanoparticles. In various embodiments, a method of making the particles comprises providing a compound disclosed herein; providing a base component (e.g., PLA-PEG or PLGA-PEG); combining the compound and the base component in an organic solution to form a first organic phase; and combining the first organic phase with a first aqueous solution to form a second phase; emulsifying the second phase to form an emulsion phase; and recovering particles. In various embodiments, the emulsion phase is further homogenized.

In some embodiments, the first phase includes about 5 to about 50% weight, e.g., about 1 to about 40% weight, or about 5 to about 30% weight, e.g., about 5%, 10%, 15%, and 20%, of the compound and the base component. In certain embodiments, the first phase includes about 5% weight of the compound and the base component. In various embodiments, the organic phase comprises acetonitrile, tetrahydrofuran, ethyl acetate, isopropyl alcohol, isopropyl acetate, dimethylformamide (DMF), methylene chloride, dichloromethane, chloroform, acetone, benzyl alcohol, Tween 80, Span 80, or a combination thereof. In some embodiments, the organic phase includes benzyl alcohol, ethyl acetate, or a combination thereof.

In various embodiments, the aqueous solution comprises water, sodium cholate, ethyl acetate, or benzyl alcohol. In some embodiments, the aqueous solution also comprises an emulsifier, including a polysorbate. For example, the aqueous solution can include polysorbate 80.

Emulsifying the second phase to form an emulsion phase may be performed in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of, e.g., probe sonicator or a high pressure homogenizer, e.g., by using 1, 2, 3 or more passes through a homogenizer. For example, when a high pressure homogenizer is used, the pressure used may be about 4000 to about 8000 psi, or about 4000 to about 5000 psi, e.g., 4000 or 5000 psi.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. Quenching may be performed at least partially at a temperature of about 5° C. or less. For example, water used in the quenching may be at a temperature that is less that room temperature (e.g., about 0 to about 10° C. or about 0 to about 5° C.).

In various embodiments, the particles are recovered by filtration. For example, ultrafiltration membranes can be used. Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (~5-25 nm) may be used.

In various embodiments, a compound of the present teachings contained within a particle is released in a controlled manner. The release can be in vitro or in vivo. For example, particles of the present teachings can be subject to a release test under certain conditions, including those specified in the U.S. Pharmacopeia and variations thereof.

In various embodiments, less than about 90%, less than about 80%, less than about 70%, less than about 60%, less than about 50%, less than about 40%, less than about 30%, or less than about 20% of the compound of the present teachings contained within particles is released in the first hour after the particles are exposed to the conditions of a release test. In some embodiments, less that about 90%, less than about 80%, less than about 70%, less than about 60%, or less than about 50% of the compound of the present teachings contained within particles is released in the first hour after the particles are exposed to the conditions of a release test. In certain embodiments, less than about 50% of the compound contained within particles is released in the first hour after the particles are exposed to the conditions of a release test.

With respect to a compound of the present teachings being released in vivo, for instance, the compound contained within a particle administered to a subject may be protected or isolated from a subject's body until the compound is released from the particle.

Thus, in some embodiments, the compound may be substantially contained within the particle until the particle is delivered into the body of a subject. For example, less than about 90%, less than about 80%, less than about 70%, less than about 60%, less than about 50%, less than about 40%, less than about 30%, less than about 20%, less than about 15%, less than about 10%, less than about 5%, or less than about 1% of the total compound is released from the particle prior to the particle being delivered into the body, for example, a treatment site, of a subject. In some embodiments, the compound may be released over an extended period of time or by bursts (e.g., amounts of the compound are released in a short period of time, followed by a periods of time where substantially no compound is released). For example, the compound can be released over 6 hours, 12 hours, 24 hours, or 48 hours. In certain embodiments, the compound is released over 1 week or 1 month.

The compound(s) may thus be contained, in large part or essentially completely within the interior of the particle, which may thus shelter it from the external environment surrounding the particle (or vice versa). For instance, a compound of the present teachings contained within a particle administered to a subject may be protected or isolated from a subject's body until the compound is released from the particle.

In further embodiments, the particle is a microparticle, nanoparticle or picoparticle. In still other embodiments, the particle is a liposome, polymeric micelle, lipoplex or polyplex, or a cyclodextrin. In some embodiments, the particle comprises one or more lipids. In some embodiments, the one or more lipids are lipidoids. In other embodiments, the particle further comprises one or more polymers. In still other embodiments, one or more of the lipids are conjugated to one or more of the polymers. In some embodiments, the particle comprises one or more polymers. In some embodiments, one or more of the lipids or polymers are degradable.

In some embodiments, the particle has an average characteristic dimension of less than about 500 nm, 400 nm, 300 nm, 250 nm, 200 nm, 180 nm, 150 nm, 120 nm, 100 nm, 90 nm, 80 nm, 70 nm, 60 nm, 50 nm, 40 nm, 30 nm, or 20 nm. In other embodiments, the particle has an average characteristic dimension of 10 nm, 20 nm, 30 nm, 40 nm, 50 nm, 60 nm, 70 nm, 80 nm, 90 nm, 100 nm, 120 nm, 150 nm, 180 nm, 200 nm, 250 nm, or 300 nm. In further embodiments, the particle has an average characteristic dimension of 10-500 nm, 10-400 nm, 10-300 nm, 10-250 nm, 10-200 nm, 10-150 nm, 10-100 nm, 10-75 nm, 10-50 nm, 50-500 nm, 50-400 nm, 50-300 nm, 50-200 nm, 50-150 nm, 50-100 nm, 50-75 nm, 100-500 nm, 100-400 nm, 100-300 nm, 100-250 nm, 100-200 nm, 100-150 nm, 150-500 nm, 150-400 nm, 150-300 nm, 150-250 nm, 150-200 nm, 200-500 nm, 200-400 nm, 200-300 nm, 200-250 nm, 200-500 nm, 200-400 nm, or 200-300 nm.

IV. Pharmaceutical Preparations

In another embodiment, a pharmaceutical composition is provided comprising the platinum compounds, complexes and/or conjugates described above, or a pharmaceutically acceptable salt thereof, in a pharmaceutically acceptable vehicle. The amount of a platinum complex or conjugate that may be combined with a pharmaceutically acceptable carrier to produce a dosage form will vary depending upon the host treated. The nanoparticulate compound may be formulated for parenteral administration by injection, e.g., by bolus injection or continuous infusion. Formulations for injection may be presented in unit dosage form in ampoules or in multi-dose containers with an optional preservative added. The parenteral preparation can be enclosed in ampoules, disposable syringes, or multiple dose vials made of glass, plastic or the like. The formulation may take such forms as suspensions, solutions, or emulsions in oily or aqueous vehicles, and may contain formulatory agents such as suspending, stabilizing, and/or dispersing agents.

For example, a parenteral preparation may be a sterile injectable solution or suspension in a nontoxic parenterally acceptable diluent or solvent (e.g., as a solution in 1,3-butanediol). Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the parenteral preparation.

Alternatively, the compositions taught herein may be formulated in powder form for reconstitution before use with a suitable vehicle, such as sterile pyrogen-free water. For example, a compound suitable for parenteral administration may comprise a sterile isotonic saline solution containing between 0.1 percent and 90 percent weight per volume of the compound. By way of example, a solution may contain from about 5 percent to about 20 percent, from about 5 percent to about 17 percent, from about 8 to about 14 percent, or about 10 percent of the compound.

V. Methods of Treating Diseases and Conditions

In additional aspects, the invention features methods of treating a disorder, e.g., a cancer or other disorder disclosed herein, in a subject in need thereof, the method comprising administering to the subject an effective amount of a platinum complex described above.

The pharmaceutical composition may comprise a plurality of particles disclosed herein that include a platinum complex in, tether to, or associated with a nanoparticle.

These and other embodiments of the present teachings may also involve the treatment of cancer or tumor according to any of the techniques and compositions and combinations of compositions described herein. In various embodiments, methods for treating a subject having a cancer are provided, wherein the method comprises administering a therapeutically-effective amount of a compound, as described herein, to a subject having a cancer or suspected of having cancer. In some embodiments, the subject may be otherwise free of indications for treatment with said compound. In some embodiments, methods include use of a therapeutically-effective amount of a compound against cancer cells, including but not limited to mammalian cancer cells. In some instances, the mammalian cancer cells are human cancer cells.

In some embodiments, a compound as described herein is a platinum compound comprising a phenanthridine ligand and has increased cytotoxicity compared to other platinum compounds (e.g., cisplatin) commonly used for the treatment of cancer.

In some embodiments, the compounds of the present teachings have been found to inhibit cancer growth, including proliferation, invasiveness, and metastasis, thereby rendering them particularly desirable for the treatment of cancer. In some embodiments, the compounds of the present teachings may be used to prevent the growth of a tumor or cancer, and/or to prevent the metastasis of a tumor or cancer. In some embodiments, compositions of the present teachings may be used to shrink or destroy a cancer.

It should be appreciated that compositions of the invention may be used alone or in combination with one or more additional anti-cancer agents or treatments (e.g., chemotherapeutic agents, targeted therapeutic agents, pseudo-targeted therapeutic agents, hormones, radiation, surgery, etc., or any combination of two or more thereof). In some embodiments, a composition of the invention may be administered to a patient who has undergone a treatment involving surgery, radiation, and/or chemotherapy. In certain embodiments, a composition of the invention may be administered chronically to prevent, or reduce the risk of, a cancer recurrence.

The cancers treatable by methods of the present teachings generally occur in mammals. Mammals include, for example, humans and other primates, as well as pet or companion animals, such as dogs and cats, laboratory animals, such as rats, mice and rabbits, and farm animals, such as horses, pigs, sheep, and cattle. In some embodiments, the compounds disclosed herein may be used to treat or affect cancers including, but not limited to, lymphatic metastases, squamous cell carcinoma, particularly of the head and neck, lung, esophageal squamous cell carcinoma, oral carcinoma, blood cell malignancies, including multiple myeloma, leukemias, including acute lymphocytic leukemia, acute non-lymphocytic leukemia, chronic lymphocytic leukemia, chronic myelocytic leukemia, and hairy cell leukemia, effusion lymphomas (body cavity based lymphomas), thymic lymphoma, lung cancer, including small cell carcinoma, non-small cell carcinoma, mesothelioma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma and triple negative carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, nerve tissue cancer, including neuroblastoma, nervous system cancers, including intrinsic brain tumors, neuroblastomaastrocytic brain tumors, gliomas, metastatic tumor cell invasion in the central nervous system, bone cancers, including osteomas and osteosarcomas, skin cancers, including malignant melanoma, tumor progression of human skin keratinocytes, squamous cell cancer, thyroid cancer, retinoblastoma, peritoneal effusion, malignant pleural effusion, gall bladder cancer, trophoblastic neoplasms, and hemangiopericytoma. In various embodiments, the cancer is lung cancer, bone cancer, breast cancer, colorectal cancer, ovarian cancer, bladder cancer, prostate cancer, cervical cancer, renal cancer, leukemia, central nerve system cancers, myeloma, and melanoma. In some cases, the cancer is lung cancer. In some cases, the cancer is human lung carcinoma.

In certain embodiments, the nanoparticles containing the platinum complexes of the present disclosure, or pharmaceutically acceptable counter ions or salts thereof, are administered in a therapeutically effective amount based on calculation of the body surface area (BSA). Such amount ranges from about 10 mg/m² BSA to about 50 mg/m² BSA administered IV wherein the mg corresponds to the total amount of platinum compound delivered per dose. In one embodiment, the therapeutically effective amount is 25 mg/m² BSA administered as a one-hour IV infusion.

The present teachings further comprise compositions (including pharmaceutical compositions) comprising any of the compounds as described herein. In some embodiments, a pharmaceutical composition is provided comprising a composition as described herein.

These and other embodiments of the present teachings may also involve promotion of the treatment of cancer or tumor according to any of the techniques and compositions and combinations of compositions described herein.

General considerations in the formulation and/or manufacture of pharmaceutical agents are known in the art and may be found, for example, in Remington: The Science and Practice of Pharmacy 21st ed., Lippincott Williams & Wilkins, 2005 (incorporated herein by reference in its entirety).

EXAMPLES

The following examples are intended to illustrate certain embodiments of the present teachings, do not exemplify the full scope of the present teachings, and therefore should not be construed to limit the scope of the present teachings.

Example 1: Synthesis of a Platinum Heterocycle Compound, 3

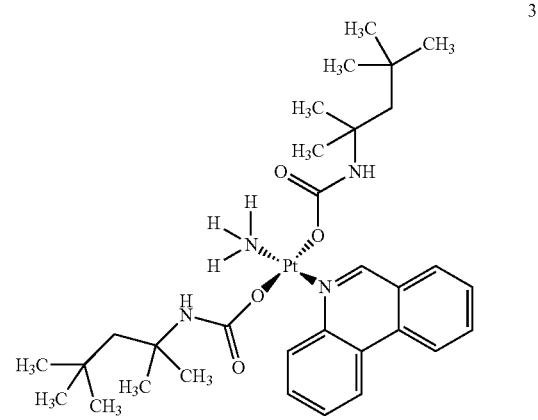

The synthetic procedure of 3 consists of three steps according to the following scheme:

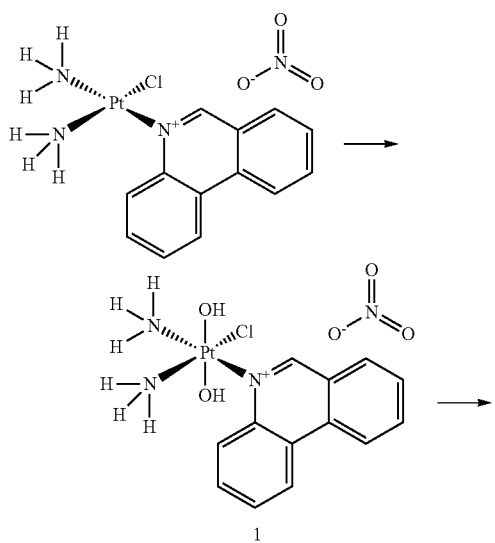

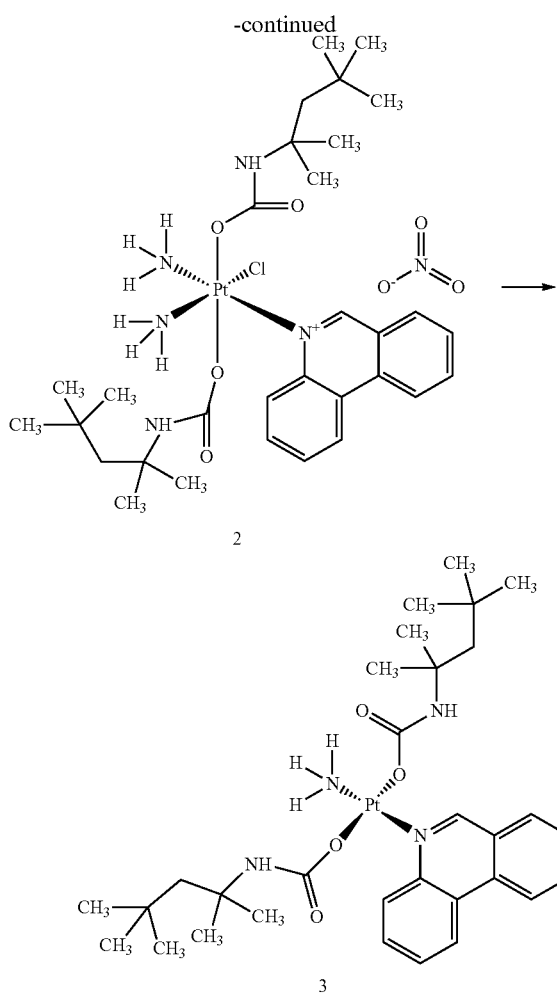

2

3

Step 1:
Phenanthriplatin (837 mg, 1.65 mmol) was suspended in hydrogen peroxide solution (30%, 5 mL) and warmed to 30° C. for 5 hours. An additional 0.5 mL of hydrogen peroxide (50%) was added and the suspension stirred for 16 hours. To the suspension was added isopropanol (8 mL) and the mixture was cooled to 4° C. for 20 hours. The solid material was isolated by filtration and dried under high vacuum at 40° C. for 16 hours to yield (700 mg, 1.3 mmol) of dihydroxyphenanthriplatin 1 (liquid chromatography-mass spectroscopy (LCMS): Rt 2.560 M$^+$477).

Step 2:
Dihydroxyphenanthriplatin 1 was suspended in N,N-dimethylformamide (10 mL) and 2-isocyanato-2,4,4-trimethylpentane (0.5 mL, 2.74 mmol) was added. The solution was stirred for 16 hours and then an additional quantity of 2-isocyanato-2,4,4-trimethylpentane (0.25 mL, 1.37 mmol) was added and the reaction stirred for an additional 16 hours. The solvent was removed under vacuum and 0.5 mL of methanol was added to dissolve the residue and tert-butylmethylether (15 mL) was added. The mixture was stored at 4° C. for 3 days resulting in a solid that was isolated by filtration. The solid was dried at 40° C. under high vacuum for 2 days resulting in 660 mg of the desired product 2 (0.8 mmol, 48% yield for 2 steps) (LCMS Rt 6.3 mins MH$^+$788).

Step 3: Compound 2 (1.10 g, 1.30 mmol) was weighed in a 100 mL round-bottom flask and dissolved in 40 mL of anhydrous dichloromethane (DCM). Triphenylphosphine resin-bound (3 mmol/g, Aldrich catalog number #366455) (1.30 g, 3.90 mmol, 3.00 equiv) was added and the reaction mixture was stirred at room temperature for 16 hours. The reaction mixture was filtered over celite and washed with DCM. The filtrate was concentrated under reduced pressure. Crude was purified using preparative HPLC (MeCN/water). Pure fractions were combined and concentrated to dryness. The resulting product was dissolved in methanol then water was added. Methanol was added until product turned into solution, then the solution was concentrated under reduced pressure to afford 3 as a white solid (510 mg, 54% yield). LCMS was used and product gave a peak RT of 6.47 minutes and (MH)$^+$ at 735, 736, 737. $^1$H NMR (d$_7$-DMF) δ 10.3-10.1 (br, 2H), 9.16 (d, J=8.3 Hz, 1H), 9.10 (d, J=8.2 Hz, 1H), 8.66-8.58 (br, 1H), 8.32 (ddd, J=7.9, 7.5, 1.2 Hz, 1H), 8.20-8.04 (br, 5H), 6.00-5.60 (br, 3H), 5.22-4.76 (br, 3H), 1.92-1.58 (br, 4H), 1.48-0.48 (br, 30H).

TABLE 1

The following analogs were prepared analogously to compound 3 starting from common intermediate 1 by using the appropriate isocyanate in step 2. The resulting platinum (IV) analogs were reduced using the same procedure as for 3.

| Compound | Structure | Retention time | Mass |
|---|---|---|---|
| 4 | [structure] | 1.813 | 623.2, 624.3, 625.3 |

TABLE 1-continued

*The following analogs were prepared analogously to compound 3 starting from common intermediate 1 by using the appropriate isocyanate in step 2. The resulting platinum (IV) analogs were reduced using the same procedure as for 3.*

| Compound | Structure | Retention time | Mass |
|---|---|---|---|
| 5 | 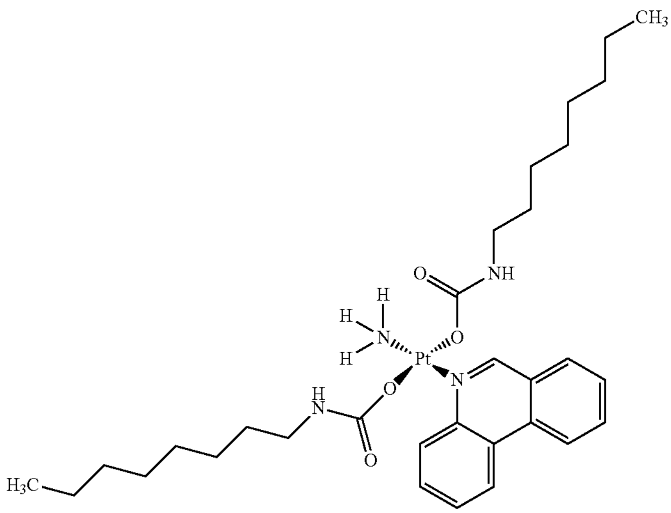 | 2.232 | 735.3, 736.3, 737.3 |
| 6 | 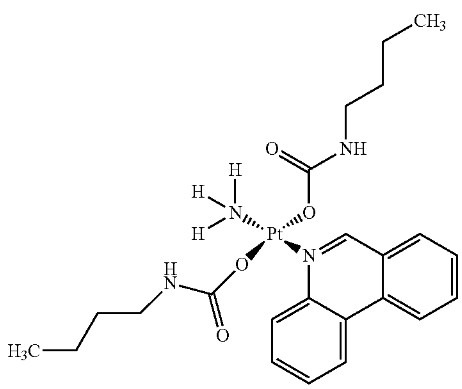 | 1.788 | 623.2, 624.2, 625.2 |
| 7 | 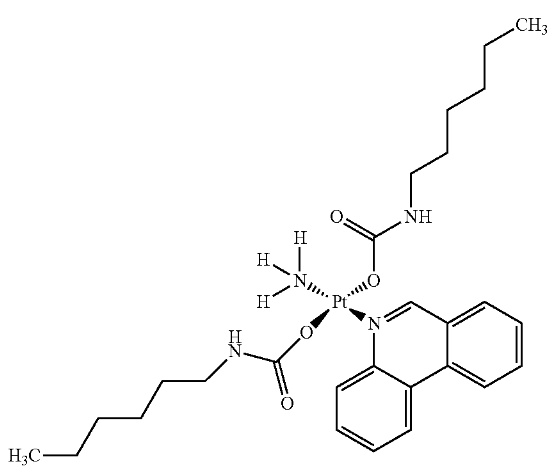 | 2.012 | 679.0, 680.0, 681.0 |

TABLE 1-continued

The following analogs were prepared analogously to compound 3 starting from common intermediate 1 by using the appropriate isocyanate in step 2. The resulting platinum (IV) analogs were reduced using the same procedure as for 3.

| Compound | Structure | Retention time | Mass |
|---|---|---|---|
| 8 | 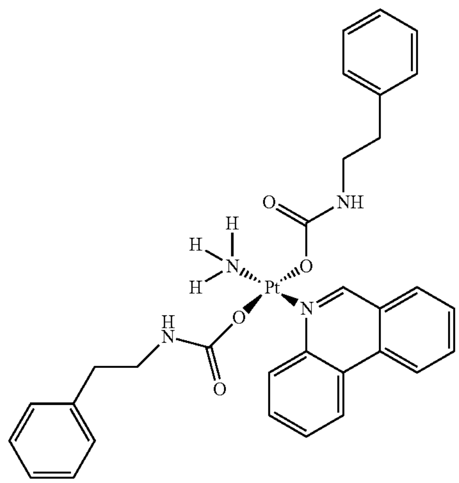 | 1.885 | 719.2, 720.3, 721.3 |
| 9 | 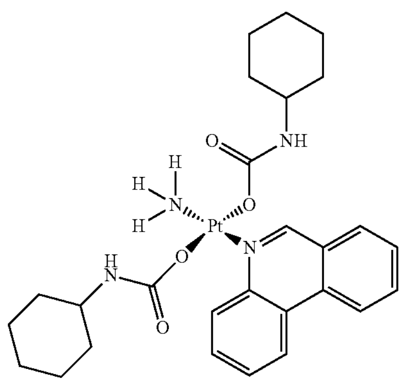 | 1.922 | 674.2, 675.2, 676.2 |

Mobile Phase: A: water (0.05% TFA) B: ACN (0.01% TFA)
Gradient: 5%-95% B in 1.4 min
Flow Rate: 2.3 ml/min, 3.2 min run
Column: SunFire C18, 4.6 * 50 mm, 3.5 um
Oven Temperature: 50 C.

Example 2: Synthesis of a Platinum Heterocycle Compound, 12

The synthetic procedure of 12 consists of three steps according to the following scheme:

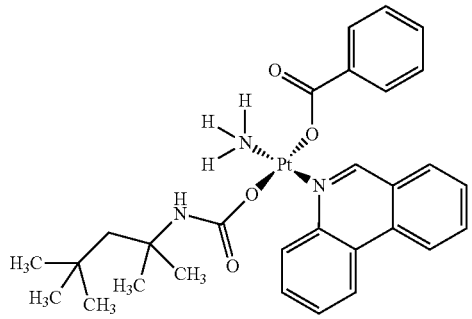

12

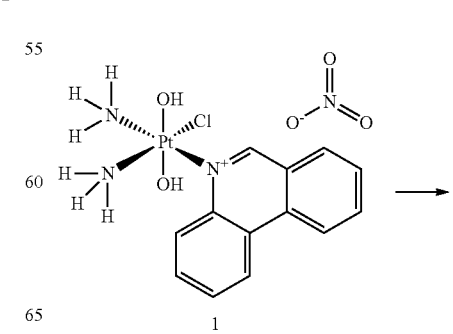

1

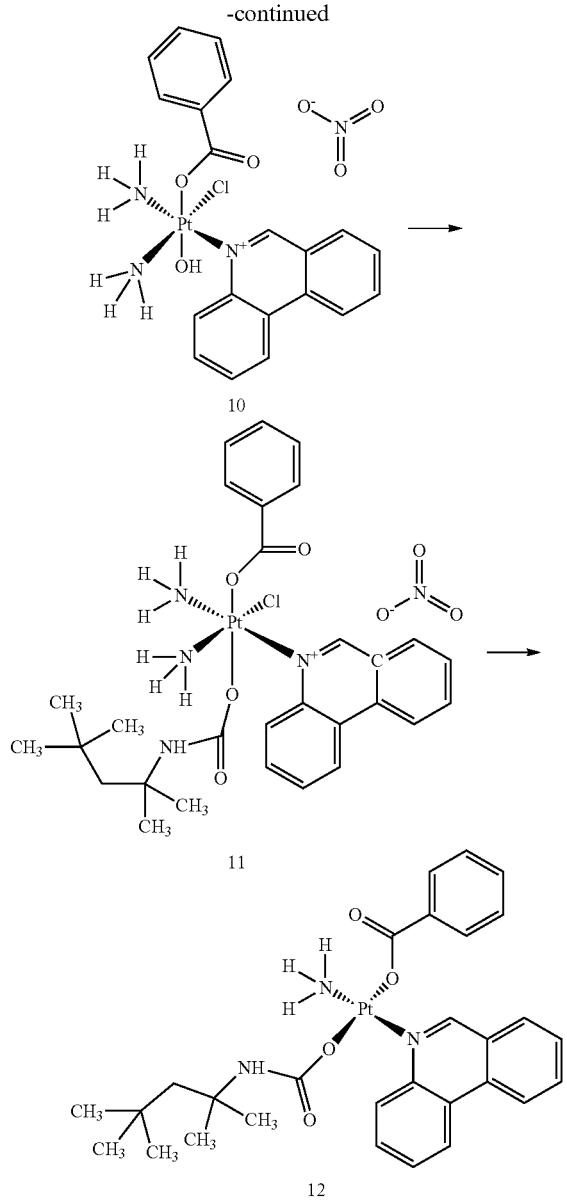

Step 1:

Dihydroxyphenanthriplatin 1 (1.6 g, 3.0 mmol) was suspended in N,N-dimethylformamide (10 mL), and benzoic anhydride (1.3 g, 5.9 mmol, 2.0 equiv) was added. The solution was stirred for 2 hours and then the solvent was removed under vacuum. 2 mL of methanol was added to dissolve the residue and then added to tert-butylmethylether (60 mL). The solid was filtered and dried under high vacuum to afford 1.0 g of the desired product 10.

Analyses: LCMS was used and product gave a peak RT of 1.387 minutes and $(MH)^+$ at 579.1, 580.1, 581.1.

Step 2:

Compound 10 (130 mg, 0.20 mmol) was dissolved in N,N-dimethylformamide (3.0 mL), and 2-isocyanato-2,4,4-trimethylpentane (120 mg, 0.80 mmol, 4.0 equiv) was added. The solution was stirred for 16 hours at 45° C. The solvent was removed under vacuum and residue was purified by reverse phase chromatography to afford 95 mg of compound 11 as a white solid.

Analyses: LCMS was used and product gave a peak RT of 1.295 minutes and $(MH)^+$ at 734.0, 735.0, 735.9.

Step 3:

Compound 11 (85 mg, 0.11 mmol) was weighed in a 8 mL vial and dissolved in 3 mL of anhydrous DCM. Triphenylphosphine resin-bound (3 mmol/g Aldrich catalog number #366455) (110 mg, 0.33 mmol, 3.0 equiv) was added and the reaction mixture was stirred at room temperature for 16 hours. The solvent was removed under vacuum and residue was purified by reverse phase chromatography to afford 8.0 mg of compound 12 as a white solid.

Analyses: LCMS was used and product gave a peak RT of 2.071 minutes and $(MH)^+$ at 684.2, 685.2, 686.2.

TABLE 2

The following analogs were prepared analogously to compound 12 starting from common intermediate 1 by using the appropriate anhydride in step 1 and isocyanate in step. 2. The resulting platinum (IV) analogs were reduced using the same procedure as for 12.

| Compound | Structure | Retention time | Mass |
|---|---|---|---|
| 13 | 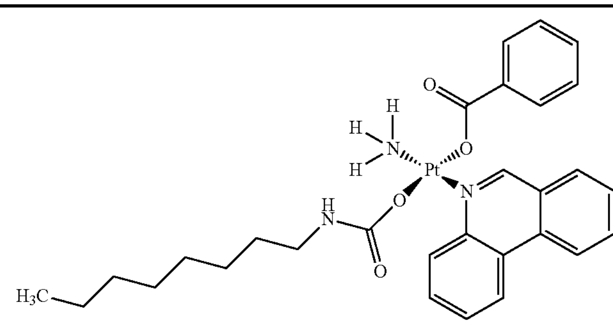 | 2.120 | 684.2, 685.2, 686.2 |

TABLE 2-continued

The following analogs were prepared analogously to compound 12 starting from common intermediate 1 by using the appropriate anhydride in step 1 and isocyanate in step. 2. The resulting platinum (IV) analogs were reduced using the same procedure as for 12.

| Compound | Structure | Retention time | Mass |
|---|---|---|---|
| 14 | 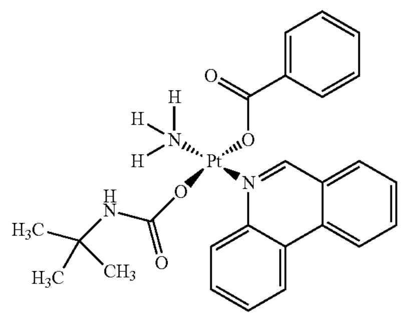 | 1.902 | 628.2, 629.2, 630.2 |
| 15 | 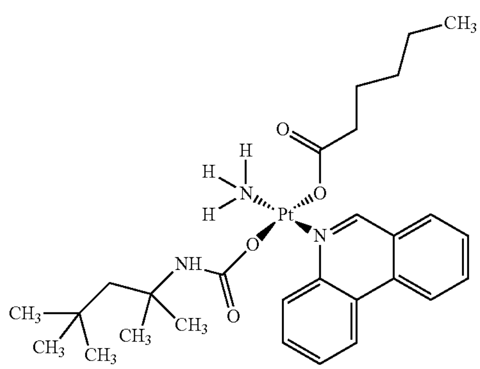 | 1.424 | 677.0, 678.0, 679.0 |
| 16 | 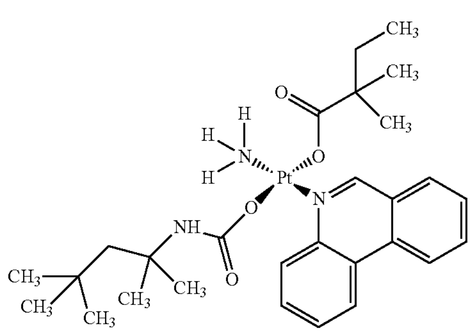 | 2.124 | 678.3, 679.3, 680.3 |

Mobile Phase: A: water (0.05% TFA) B: ACN (0.01% TFA)
Gradient: 5%-95% B in 1.4 min
Flow Rate: 2.3 ml/min, 3.2 min run
Column: SunFire C18, 4.6 * 50 mm, 3.5 um
Oven Temperature: 50 C.

Example 3: Synthesis of a Platinum Heterocycle Compound, 17

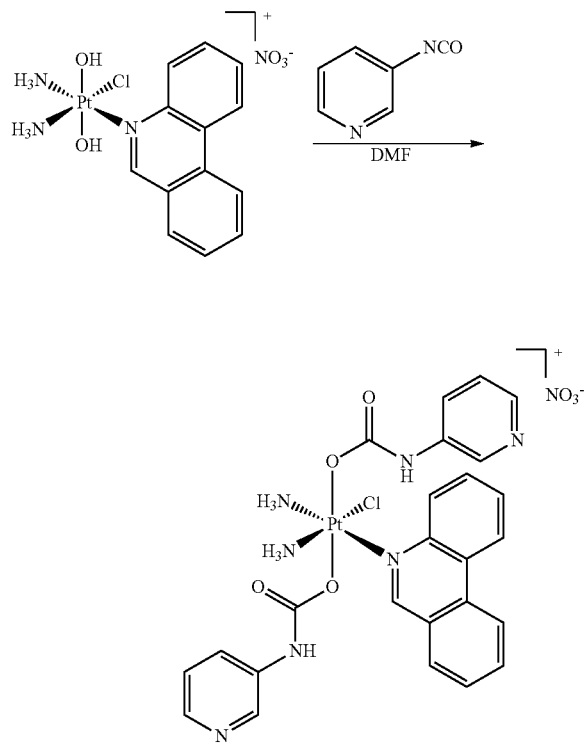

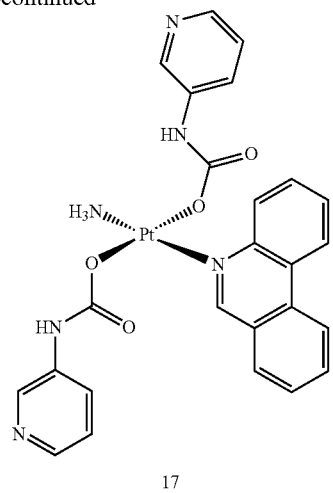

Di-3-pyridinecarbamate, di-ammonia, chloro phenanthriplatinium (IV): Di-hydroxy phenanthriplatin (130 mg, 0.24 mmol, 1.0 equiv) was suspended in DMF (1.8 mL) and was added 3-pyridine isocyanate (57.9 mg, 0.48 mmol, 2.0 equiv). The reaction mixture was stirred at room temperature for 2 hours. The reaction mixture was concentrated to dryness and the residue was triturated with dichloromethane to provide the titled compound (172 mg, 91% yield); HPLC-MS 91.4% m/z for $C_{25}H_{25}ClN_7O_4Pt$ [(M+H)+]=718.5.

Di-3-pyridinecarbamate, ammonia phenanthriplatinium (II): Di-3-pyridinecarbamate di-ammonia chloro phenanthriplatinium (IV) (100 mg, 0.128 mmol, 1.0 equiv) was suspended in dichloromethane (4.0 mL) and treated with triphenylphosine resine bound (loading 3 mmol/g, 128 mg, 0.384 mmol, 3.0 equiv). The reaction mixture was stirred at room temperature for 48 hours. The reaction mixture was diluted with methanol and filtered over filter paper. The filtrate was evaporated in vacuo. The residue was adsorbed on silica gel and purified using a silica gel column (12 g), eluted using 0-20% MeOH/CH$_2$Cl$_2$ gradient over 20 minutes. Fractions containing the product were concentrated and the residue was diluted with MeCN/H$_2$O and lyophilized to provide the product as a yellow solid (8.4 mg, 9% yield); $^1$H NMR (500 MHz, DMF-d$_7$) δ 10.14-10.10 (m, 2H), 9.02 (d, 1H, J=8.2 Hz), 8.97 (dd, 1H, J=8.3 Hz, J=1.1 Hz), 8.59-8.49 (m, 5H), 8.22-8.16 (m, 1H), 8.06-7.95 (m, 4H), 7.94-7.89 (m, 1H), 7.86-7.76 (m, 2H), 7.12-7.01 (m, 2H), 5.41 (s, 3H); HPLC-MS 93%. m/z for $C_{25}H_{22}N_6O_4Pt$ [(M+H)+]=666.6.

Example 4: Synthesis of a Platinum Heterocycle Compound, 18

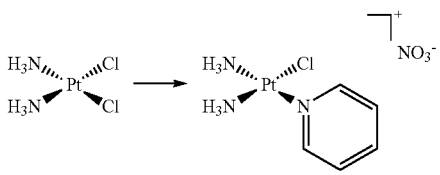

Di-ammonia, chloro pyridiniplatinium (II): In a 250 ml round bottom flask was added cisplatin (1.50 g, 5.00 mmol, 1.0 equiv) and silver nitrate (1.10 g, 6.50 mmol, 1.3 equiv). DMF (100 mL) was added and the flask was covered with foil. The reaction mixture was stirred at 55° C. for 16 hours. The AgCl precipitate was filtered off at room temperature using a Buchner funnel. To the filtrate was added pyridine (356 mg, 4.50 mmol, 0.9 equiv), the flask was covered with foil and heated at 55° C. for 16 hours. The reaction mixture was concentrated and filtered using a Buchner funnel and washed with methanol. The filtrate was concentrated and triturated with CH$_2$Cl$_2$ 16 hours in a sonic bath. A grey solid was obtained. A second trituration was done with DMF and

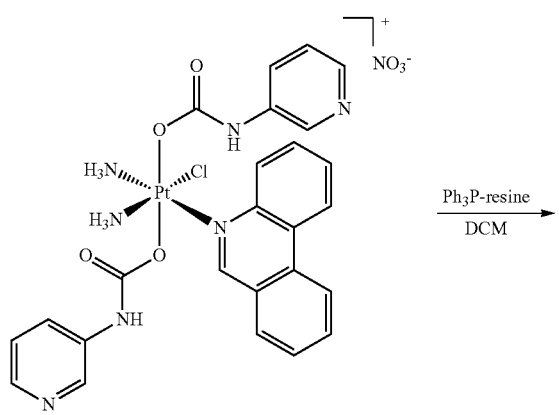

dichloromethane to afford the titled compound (1.07 g, 53% yield, purity by $^1$H NMR 72%); $^1$H NMR (500 MHz, DMF-$d_7$) δ 8.88-8.85 (m, 2H), 8.14-8.08 (m, 1H), 7.65-7.60 (m, 2H), 5.00 (s, 3H), 4.53 (s, 3H).

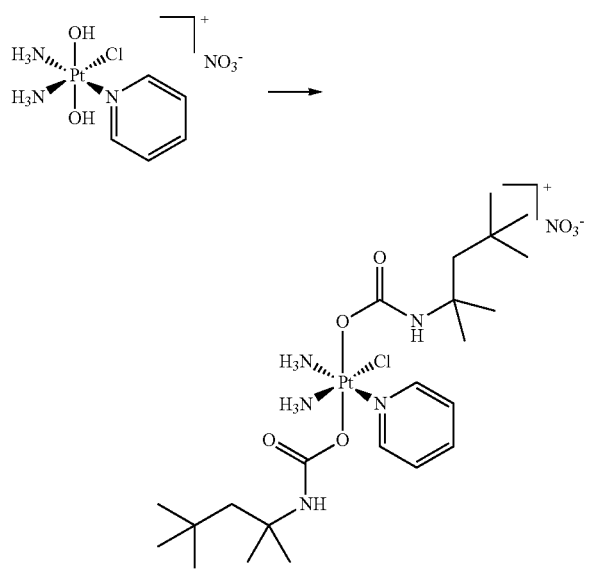

Di-hydroxy, di-ammonia, chloro pyridiniplatinium (IV): Di-ammonia, chloro pyridiniplatinium (II) (100 mg, 0.246 mmol, 1.0 equiv) was dissolved in a mixture of t-butanol (1.33 mL) and water (0.68 mL) followed by the addition of m-CPBA (110 mg, 0.493 mmol, 2.0 equiv) and the reaction mixture was stirred at room temperature for 16 hours. The reaction mixture was diluted with water and dichloromethane and the layers were separated. The aqueous layer was extracted twice with dichloromethane and the combined organic layers were concentrated. The residue was triturated with methanol and CH$_2$Cl$_2$, to afford the titled compound as an off-white solid to (68.2 mg, 63% yield); $^1$H NMR (500 MHz, DMF-$d_7$) δ 9.33-9.25 (m, 2H), 8.30-8.25 (m, 1H), 7.86-7.81 (m, 2H), 6.40-6.00 (m, 6H); HPLC-MS 98.2%. m/z for C$_5$H$_{13}$ClN$_3$O$_2$Pt [(M+H)+]=377.3.

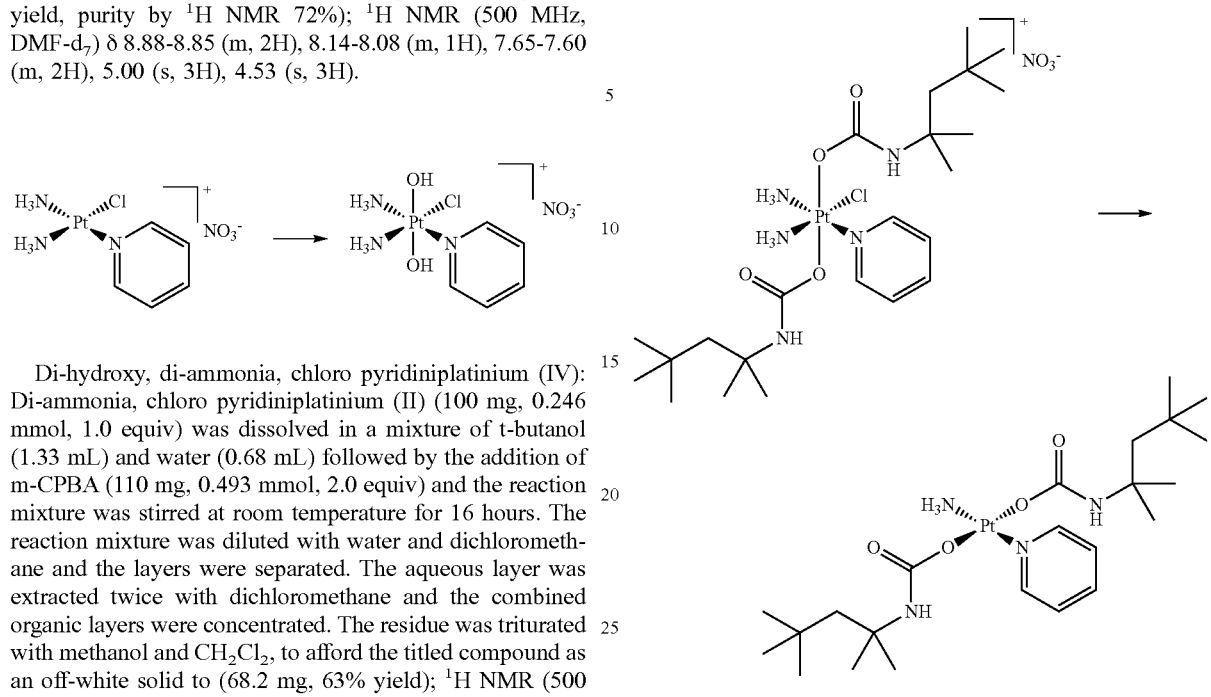

Di-1,1,3,3-tetramethylbutylcarbamate, di-ammonia, chloro pyridiniplatinium (IV): Di-hydroxy, di-ammonia, chloro pyridiniplatinium (IV) (250 mg, 0.569 mmol, 1.0 equiv) was dissolved in DMF (5.7 mL) and was added the 1,1,3,3-tetramethylbutylisocyanate (530 mg, 3.41 mmol, 6.0 equiv). The reaction mixture was stirred at RT for 64 hours before it was diluted with EtOAc and washed three times with water and the organic layer was concentrated. The residue was triturated with CH$_2$Cl$_2$ to afford the titled compound as a yellow solid (109 mg, 26% yield); HPLC-MS 98.9% m/z for C$_{23}$H$_{47}$ClN$_5$O$_4$Pt [(M+H)+]=688.6

Di-1,1,3,3-tetramethylbutylcarbamate, ammonia pyridiniplatinium (II): To a solution of di-1,1,3,3-tetramethylbutylcarbamate, di-ammonia, chloro pyridiniplatinium (IV) (25 mg, 0.033 mmol, 1.0 equiv) in methanol (3 mL) was added a solution of glutathione (20.3 mg, 0.066 mmol, 2.02 equiv) in phosphate buffer pH 8 (3 mL). The reaction mixture was stirred at room temperature over the weekend, before it was concentrated and dissolved in 1/1 MeOH/H$_2$O (2 mL). The solution was purified by semi-prep HPLC, column X-Terra 5 um, 30×50 mm, eluted with 40-55% MeCN—H2O in 10 minutes, flow 45 mL/min. Fractions containing the product were combined and lyophilized to provide the title compound as an off-white solid (8.0 mg, 38% yield); $^1$H NMR (500 MHz, DMF-$d_7$) δ 8.84-8.77 (m, 2H), 8.11-8.06 (m, 1H), 7.54-7.46 (m, 2H), 5.76-5.37 (m, 5H), 1.67 (bs, 4H), 1.25 (s, 12H), 0.96 (s, 18H); HPLC-MS 100% m/z for C$_{23}$H$_{44}$N$_4$O$_4$Pt [(M+H)+]=636.7

Example 5: Synthesis of a Platinum Heterocycle Compound, 19

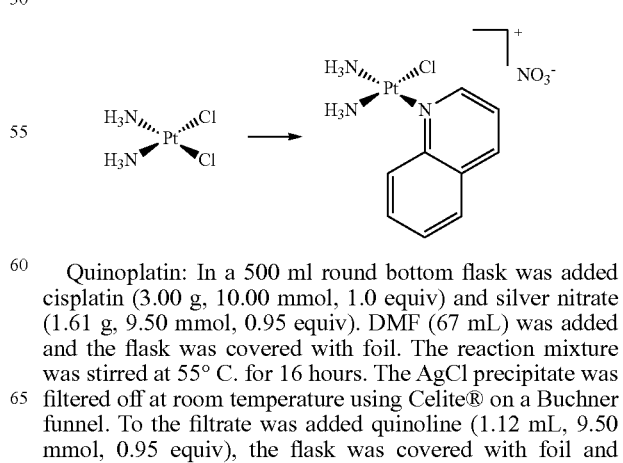

Quinoplatin: In a 500 ml round bottom flask was added cisplatin (3.00 g, 10.00 mmol, 1.0 equiv) and silver nitrate (1.61 g, 9.50 mmol, 0.95 equiv). DMF (67 mL) was added and the flask was covered with foil. The reaction mixture was stirred at 55° C. for 16 hours. The AgCl precipitate was filtered off at room temperature using Celite® on a Buchner funnel. To the filtrate was added quinoline (1.12 mL, 9.50 mmol, 0.95 equiv), the flask was covered with foil and heated at 55° C. for 16 hours. The reaction was cooled to RT and filtered with Celite on a Buchner funnel, washed with DMF and concentrated to dryness. The residue was triturated in MeOH to afford the title compound as a white solid (2.47 g, 54% yield; $^1$H NMR (500 MHz, DMF-d$_7$) δ 9.68 (d, J=8.7 Hz, 1H), 9.43 (dd, J=5.3, 1.5 Hz, 1H), 8.75 (d, J=8.3 Hz, 1H), 8.21 (d, J=8.2 Hz, 1H), 8.07 (ddd, J=8.6, 6.9, 1.4 Hz, 1H), 7.83 (ddd, J=8.0, 7.0, 1.0 Hz, 1H), 7.74 (dd, J=8.3, 5.3 Hz, 1H), 5.20-4.82 (br s, 3H), 4.82-4.40 (br s, 3H).

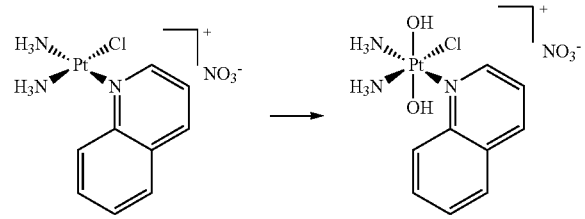

Di-hydroxy, di-ammonia, chloro quinoliplatinium (IV): quinoplatin (1.40 g, 3.45 mmol, 1.0 equiv) was dissolved in a mixture of t-butanol (47 mL) and water (23 mL) followed by the addition of m-CPBA (1.55 g, 6.90 mmol, 2.0 equiv). The reaction mixture was stirred at room temperature for 16 hours. The reaction mixture was concentrated to dryness. The residue was triturated in a methanol/MTBE mixture to afford the titled compound (1.33 g, 87% yield).

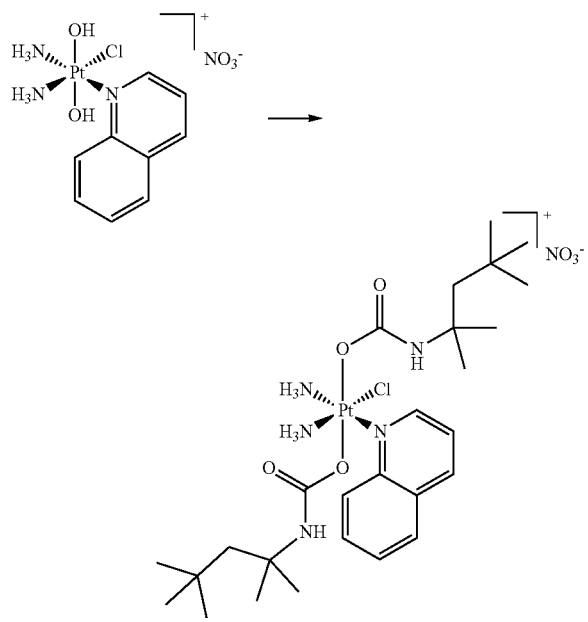

Di-1,1,3,3-tetramethylbutylcarbamate, di-ammonia, chloro quinoplatinium (IV): Di-hydroxy, di-ammonia, chloro quinoplatinium (IV) (1.30, 2.65 mmol, 1.0 equiv) was dissolved in DMF (27 mL) and was added the 1,1,3,3-tetramethylbutylisocyanate (2.47 g, 15.9 mmol, 6.0 equiv). The reaction mixture was stirred at room temperature for 64 hours before it was diluted with EtOAc and washed three times with water, washed with brine and concentrated. The residue was triturated with CH$_2$Cl$_2$ to afford the titled compound as a yellow solid (1.07 g, 50% yield); $^1$H NMR (500 MHz, DMF-d$_7$) δ 9.37 (s, 1H), 9.00 (m, 1H), 8.30 (d, J=8.1 Hz, 1H), 8.00-7.23 (m, 8H), 6.60 (s, 1H), 1.80-1.40 (m, 4H), 1.37-1.05 (m, 12H), 0.95 (s, 18H); HPLC-MS 99.3% m/z for C$_{27}$H$_{49}$ClN$_5$O$_4$Pt [(M+H)+]=738.66.

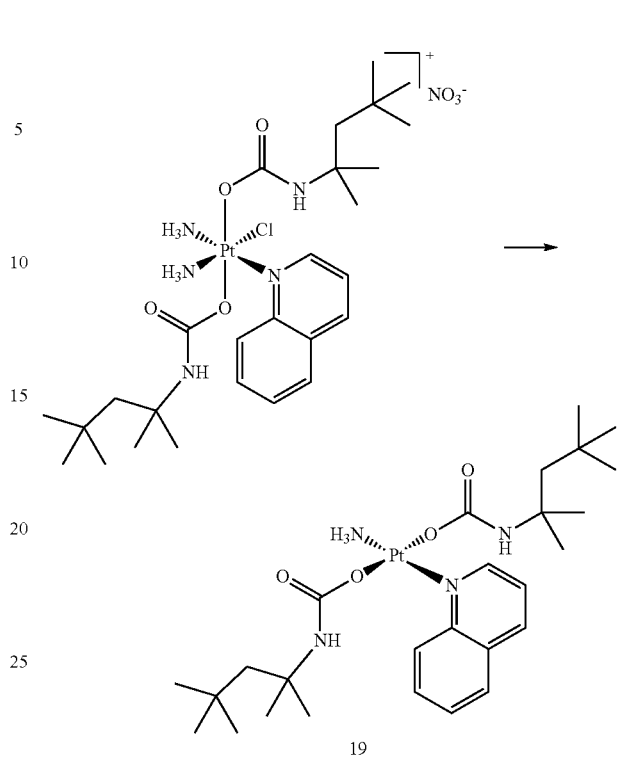

Di-1,1,3,3-tetramethylbutylcarbamate, ammonia quinoplatinium (II): To a solution of di-1,1,3,3-tetramethylbutylcarbamate, di-ammonia, chloro quinoplatinium (IV) (1.00 g, 1.25 mmol, 1.0 equiv) in CH$_2$Cl$_2$ (25 mL) was added triphenylphosphine PS-supported 3 mmol/g (1.00 g, 3.75 mmol, 3.00 equiv). The reaction mixture was stirred at RT for 3 hours, filtered on a Buchner funnel and concentrated. The residue was purified on silica (gradient 0-20% MeOH/CH$_2$Cl$_2$) to provide the title compound as an off-white solid (114 mg, 22% yield); $^1$H NMR (500 MHz, DMF-d$_7$) δ 10.05-9.20 (m, 1H), 8.70 (d, J=8.3 Hz, 1H), 8.15 (d, J=8.1 Hz, 1H), 8.05-7.95 (m, 2H), 7.78 (t, J=7.5 Hz, 1H), 7.69 (m, 1H), 5.80-4.50 (m, 5H), 1.80-0.40 (m, 34H); HPLC-MS 100% m/z for C$_{27}$H$_{46}$N$_4$O$_4$Pt [(M+H)+]=686.75.

Example 6: Effect of Platinum Heterocycle Compounds on Tumor Cells

The effect of compounds described herein on tumor cells was determined using tumor cell lines.

For cell seeding, a complete medium was prepared by adding fetal bovine serum (FBS) and the appropriate additives and mixing gently. The culture medium was removed and discarded using a vacuum pump. The cell layer was briefly rinsed with 0.25% (w/v) trypsin-0.038% (w/v) EDTA solution to remove all traces of serum, which contains trypsin inhibitor. A trypsin-EDTA solution (3.0 mL) was added to a flask of cultured cells and the cells were observed under an inverted microscope until the cell layer dispersed. 8.0 mL of complete growth medium was then added and cells were aspirated by gentle pipetting. The cell suspension was transferred to a centrifuge tube and centrifuged at 800-1000 rpm for 3-5 minutes. The supernatant was discarded using a vacuum pump. An appropriate volume of complete medium was added, and the cell pellet was suspended by gentle pipetting. The cell numbers were counted and the cells were adjusted to the appropriate concentration. 100 μL of cell suspension was added to 96-well white-walled clear bottom plates and placed in the CO$_2$ incubator overnight.

For compound plate preparation and addition, compounds were prepared from 2 mM DMSO stock with 3-fold dilution (200-fold of the final concentration). About 0.5 to 1 uL of the compound was transferred from the compound plates to the cell plates. The plates were incubated for the indicated time at 37° C.

A luminescent assay, CellTiter®-Glo (Promega, Madison, Wis.) was used to assay cell viability, essentially according to the manufacturer's instructions. To prepare the reagents for assaying the effect of compounds on the cells, CellTiter-Glo buffer was thawed and equilibrated to room temperature prior to use. The lyophilized CellTiter-Glo substrate was equilibrated to room temperature prior to use. The appropriate volume of CellTiter-Glo Buffer was transferred into the amber bottle containing the CellTiter-Glo substrate to reconstitute the lyophilized enzyme/substrate mixture to form the CellTiter-Glo Reagent. The CellTiter-Glo Reagent was mixed by gently vortexing, swirling or by inverting the contents to obtain a homogeneous solution. The CellTiter-Glo Substrate went into solution easily in less than one minute.

For luminescence measurements, cell morphology was observed under an inverted microscope. The plate and its contents were equilibrated to room temperature for approximately 30 minutes. 100 µL of CellTiter-Glo Reagent was then added to the assay plate. The contents were mixed for 2 minutes on an orbital shaker to induce cell lysis. The plate was allowed to incubate at room temperature for 10 minutes to stabilize luminescent signal. The clear bottom was pasted with white back seal and the luminescence was recorded with Flexstation3. The settings were: Luminescence, integration time 500 ms.

As assayed, each of the compounds below has an $IC_{50}$ in the A549 tumor cell line as shown below.

| Compound | A549 $IC_{50}$ (µM) |
|---|---|
| 3 | 0.04 |
| 5 | 0.126 |
| 6 | 3.87 |
| 7 | 1.25 |
| 8 | 2.36 |
| 9 | 14.7 |
| 12 | 0.098 |
| 13 | 0.115 |
| 14 | 1.43 |
| 15 | 0.18 |
| 16 | 0.225 |
| 19 | 4.3 |

These data demonstrate that the compounds described herein are potent inhibitors of proliferation of a lung cancer cell line.

Example 7: Platination with 2'-Deoxyguanosine 5'-monophosphate (GMP)

Compound 3 (0.38 mg, 0.0050 mmol) was weighed in an HPLC vial and dissolved in 200 µL of methanol. 2'-Deoxyguanosine 5'-monophosphate disodium salt hydrate (GMP) (2.0 mg, 0.050 mmol, 10 equiv) was dissolved in 200 µL of PBS pH 7 buffer solution and then added to the methanol solution. The reaction was monitored by HPLC/MS for disappearance of starting material. After stirring at 24 hours at room temperature, the starting material was intact and no platinum-GMP adduct could be detected. The solution was warmed to 37° C. for 1.5 hours, after which no platinum-GMP was formed and only starting material could be detected.

This experiment demonstrates that this class of compounds has unexpected properties in their in ability to react with a DNA base despite being a potent inhibitor of cell proliferation.

Example 8: DNA Association Assay of a Compound

To examine the unexpected property of a compound of the present invention, compound 3 was incubated with DNA and the amount of platinum associated with the DNA determined. Briefly, calf thymus DNA was obtained from Fisher Scientific and was solubilized to 1 mg/mL in 18 ohm water. Compound was spiked into this solution to 60 µM and incubated at 37° C. for 2 hours. The DNA was then run through a DNEasy™ (Qiagen, Valencia, Calif.) DNA purification kit so that the resulting concentrate would be similar to that obtained from other sources, and to separate bound platinum from unbound platinum. The resulting extract was then analyzed by GFAA (graphite furnace atomic absorption) for platinum content. This analysis showed that the isolated DNA had no platinum associated with it.

This result is very unexpected for a potent platinum(II) inhibitor of cell proliferation. Classic platinum agents such as cisplatin show a high degree of DNA associated platinum in this type of experiment.

Example 9: DNA Platination in Cells

DNA platination from incubation of compound 3 in A549 cells. $5 \times 10^6$ A549 cells were received in tubes from Nobel Life Sciences in 10% FBS, 5% DMSO. Upon thawing, cells were washed with RPMI to remove the DMSO. Cells were then incubated for 2 hours at 37° C. with 60 µM compound 3 or cisplatin. Cells were then lysed and applied to a DNEasy™ DNA purification kit. The resulting DNA extracts were then analyzed by GFAA.

| Sample | % of Cisplatin standard |
|---|---|
| Blank | 1% |
| Compound 3 | 37% |
| Cisplatin | 100% |

This experiment shows that, in contrast to the results of Example 8 in which a compound was incubated in the presence of DNA, in the presence of a tumor cell line compound 3 is bioactivated into a form that platinates DNA.

Example 10: Nanoparticles Containing a Platinum Heterocycle Compound

Compound 3 nanoparticles were prepared by homogenizing an oil in water emulsion that was subsequently purified via tangential flow filtration (TFF). Three nanoparticle formulations were prepared by varying the polymer molecular weight (MW) and/or the polymer type. The two types of polymer were either poly (L-lactic acid) (PLAmPEG) or 7525 poly(lactic-co-glycolic acid) (7525 PLGAmPEG) with the mPEG indicating that a methoxy-polyethylene glycol chain is coupled to the end of the polymer chain hence making it a PEGylated polymer. The molecular weight of the PL(G)A portion was varied between 15 kD and 35 kD with the PEG chain kept constant at 5 kD. In the emulsion, the oil phase consisted of the polymer dissolved in ethyl acetate to achieve a concentration of 50 mg/mL and 3 was added to reach a concentration of 5.56 mg/ml (target drug load of 10% w/w). The oil phase was then slowly added to the aqueous phase and mixed by a rotor-stator homogenizer to form a coarse emulsion (10/90% v/v oil/water). The coarse emulsion was then processed through a high-pressure homogenizer (operated at 10,000 psi for 2 passes) to form a nanoemulsion. The nanoemulsion was hardened by quenching (5-fold dilution in deionized water) to form a nanoparticle (NP) suspension. This suspension was further diluted to make a 10-fold dilution (of the initial emulsion) which was then concentrated and purified with deionized water using tangential flow filtration (TFF, 500 kDa MWCO membrane).

In vitro and in vivo properties of the nanoparticle suspension are summarized in Table 1. Particle size (z.ave) and the polydispersity index (PDI) were characterized by dynamic light scattering. The actual drug load was determined by gravimetric analysis: 1 mL of the nanoparticle suspension was transferred to a 4 mL glass vial and dried under vacuum (rotary evaporator) to remove the dispersion medium (water and residual solvents from the process). The total amount of solids was determined based on the weights of the empty vial and the vial containing the dried sample. Drug content was then determined by graphite furnace atomic absorption spectroscopy. Based on of these analyses, the drug load was calculated by the weight of active drug divided by weight of the solids. Encapsulation efficiency was defined as the ratio between the actual and target drug load. Target drug load was calculated based on of the measured active drug concentration of the oil phase used for encapsulation.

In vitro dissolution studies were carried out at 37° C. in a shaking water bath. Nanoparticle suspensions were added to a float-a-lyzer dialysis membrane (1000 kD MWCO) and 60 ml of 0.1% hexadecyltrimethylammonium bromide (CTAB) in phosphate buffered saline (PBS) was used as a sink condition. Table 1 indicates the cumulative release of 2 nanoparticle suspensions after 6 hours of dissolution. In vivo dissolution was carried out in a rat PK model administered via tail vein injection. These data demonstrate that a compound disclosed herein can be encapsulated in nanoparticles.

TABLE 1

In vitro and in vivo PK properties of the nanoparticle suspensions

| Formulation | Compound 3 NP001 | Compound 3 NP002 | Compound 3 NP003 |
|---|---|---|---|
| Polymer | $PLA_{15}mPEG_5$ | $PLA_{35}mPEG_5$ | $7525PLGA_{15}mPEG_5$ |
| Emulsifier | None | 0.2% Polysorbate 80 | None |
| Z-ave, nm | 117* | 84* | 101 |
| PDI | 0.20* | 0.16* | 0.27 |
| Actual drug load (ADL) (%) | 7.7* | 7.3* | 8.2 |
| Encapsulation Efficiency, EE (%) | 71* | 60* | 68 |
| In vitro release at 6 hr | 41.8* | 40.8 | Not available |
| AUC (µM/L · hr) | 36.1 | 36.1 | Not available |
| $t_{1/2}$ (hr) | 14.6 | 13.5 | Not available |

*Average of 2 batches

EQUIVALENTS AND SCOPE

While several embodiments of the present teachings have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present teachings. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present teachings is/are used. Those skilled in the art will recognize, or be able to ascertain using no more than routine experimentation, many equivalents to the specific embodiments of the present teachings described herein. It is, therefore, to be understood that the foregoing embodiments are presented by way of example only and that, within the scope of the appended claims and equivalents thereto, the present teachings may be practiced otherwise than as specifically described and claimed. The present teachings are directed to each individual feature and/or method described herein. In addition, any combination of two or more such features and/or methods, if such features and/or methods are not mutually inconsistent, is included within the scope of the present teachings.

The above description of the disclosed embodiments is provided to enable any person skilled in the art to make or use the invention disclosed herein. Various modifications to these embodiments will be readily apparent to those skilled in the art, and the generic principles described herein can be applied to other embodiments without departing from the spirit or scope of the invention. Thus, it is to be understood that the description and drawings presented herein are representative of the subject matter which is broadly contemplated by the present invention. It is further understood that the scope of the present invention is not intended to be limited to the embodiment shown herein but is to be accorded the widest scope consistent with the patent law and the principles and novel features disclosed herein.

Alternative embodiments of the claimed disclosure are described herein. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of inhibiting proliferation of a lung cancer cell comprising contacting the cell with an effective amount of a compound selected from a group consisting of:

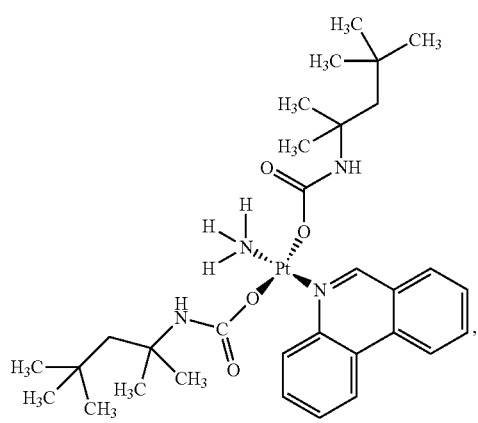
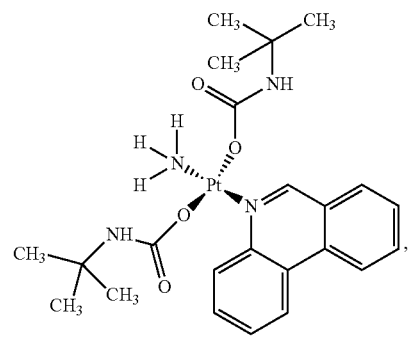
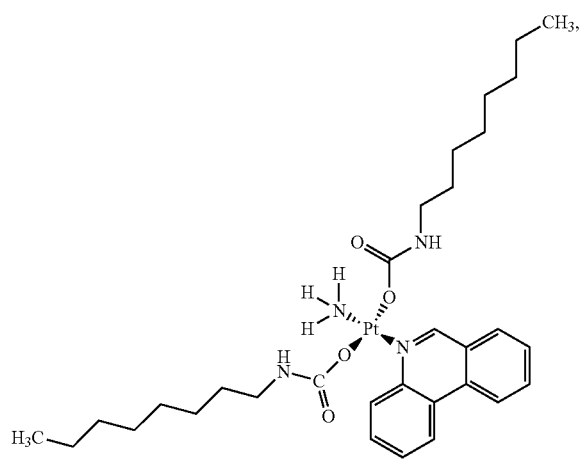
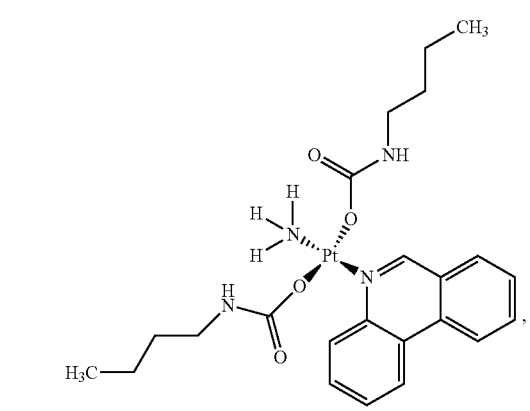
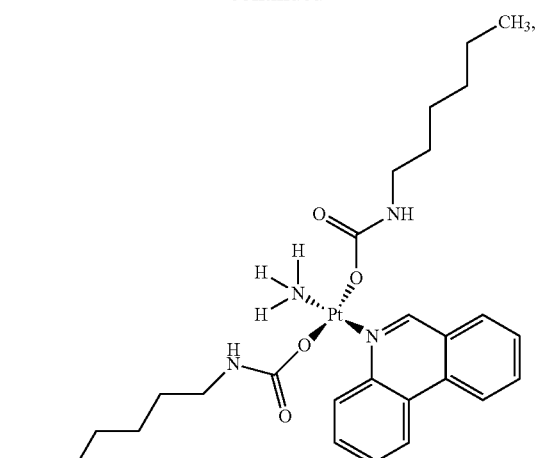
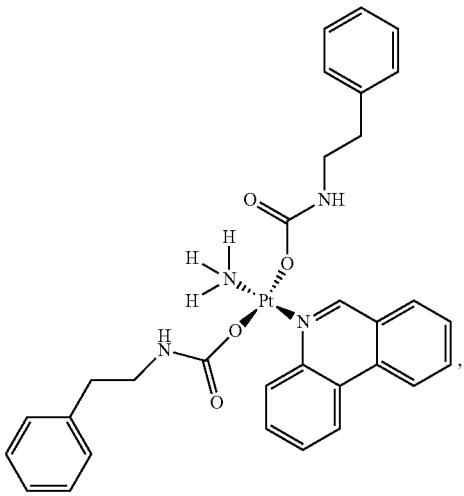
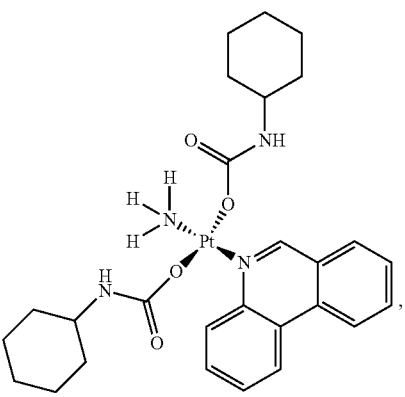

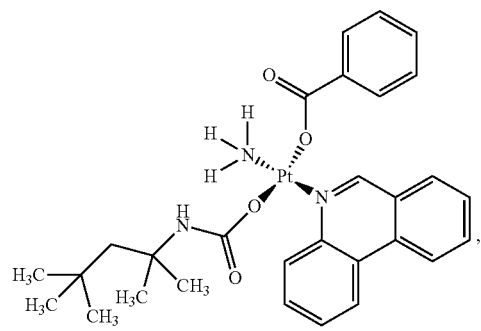
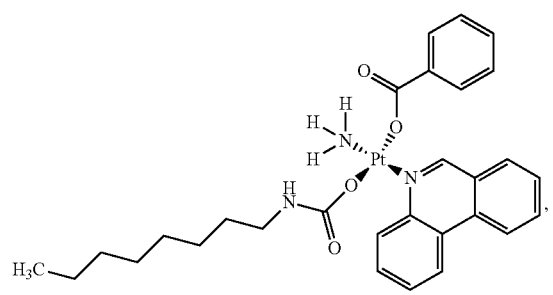
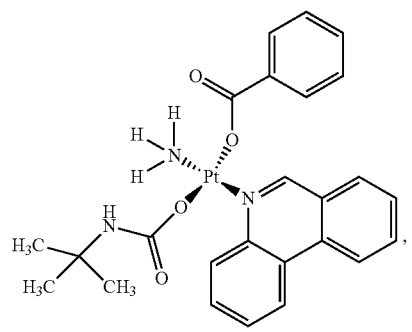
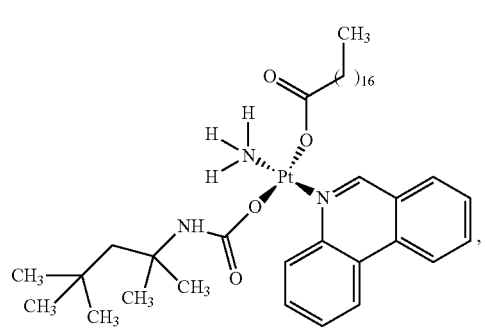
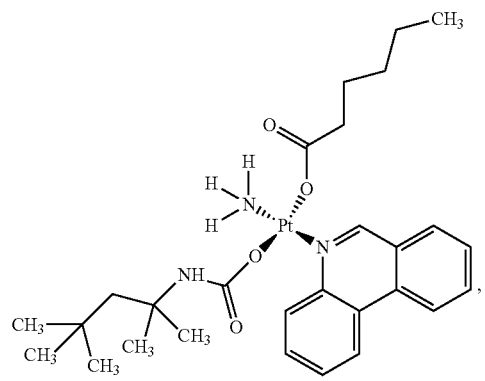
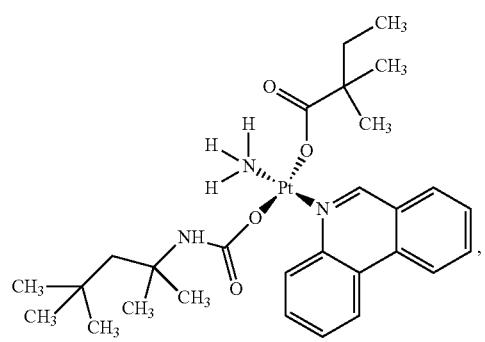
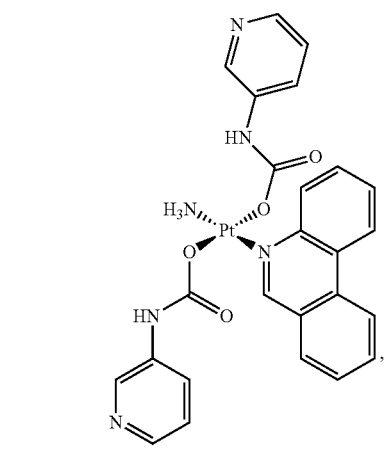
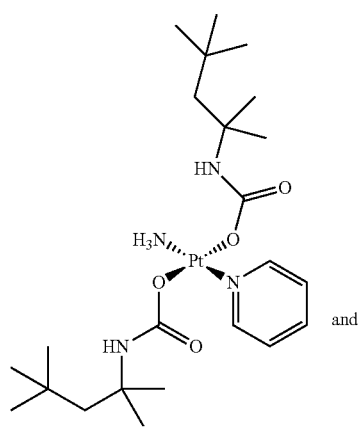

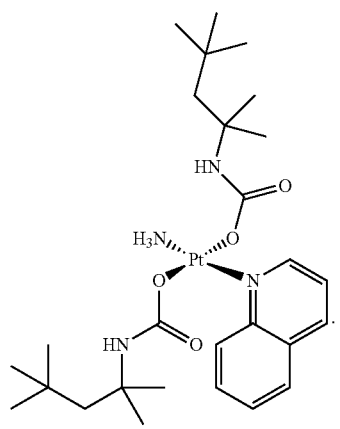
* * * * *